(12) United States Patent
Long et al.

(10) Patent No.: US 7,879,042 B2
(45) Date of Patent: Feb. 1, 2011

(54) SURFACE REPLACEMENT EXTRACTOR DEVICE AND ASSOCIATED METHOD

(75) Inventors: Jack F. Long, Warsaw, IN (US); Robert VonZabern, Riverside, CA (US)

(73) Assignee: Depuy Products, Inc., Warsaw, IN (US)

( * ) Notice: Subject to any disclaimer, the term of this patent is extended or adjusted under 35 U.S.C. 154(b) by 110 days.

(21) Appl. No.: 10/794,620

(22) Filed: Mar. 5, 2004

(65) Prior Publication Data

US 2005/0209597 A1    Sep. 22, 2005

(51) Int. Cl.
 *A61B 17/88* (2006.01)
 *A61F 2/36* (2006.01)
(52) U.S. Cl. .................... 606/99; 623/22.12
(58) Field of Classification Search ............. 606/86, 606/99, 91, 86 R; 623/20.35, 22.11, 22.12, 623/22.15, 23.11, 23.12
 See application file for complete search history.

(56) References Cited

U.S. PATENT DOCUMENTS

| 788,362 A | 4/1905 | Lavery |
| 1,023,542 A | 4/1912 | Winter |
| 1,345,443 A | 7/1920 | Hood |
| 1,669,701 A | 2/1926 | Estwing |
| 2,243,718 A | 11/1938 | Moreira |
| 2,222,517 A | 12/1938 | Price |
| 2,200,120 A | 5/1940 | Nauth |
| 2,718,228 A | 9/1955 | Van Steenbrugghe |
| 2,725,878 A | 12/1955 | Woodside |
| 2,804,895 A | 9/1957 | Clement |
| 2,934,065 A | 4/1960 | Townley |
| 3,002,514 A | 10/1961 | Deyerle |
| 3,605,527 A | 9/1971 | Gambale |
| 3,702,611 A | 11/1972 | Fishbein |
| 3,840,904 A | 10/1974 | Tronzo |
| 3,855,638 A | 12/1974 | Pilliar |
| 3,979,778 A | 9/1976 | Stroot |
| 4,042,980 A | 8/1977 | Swanson et al. |
| 4,206,517 A | 6/1980 | Pappas et al. |
| 4,271,849 A | 6/1981 | Rehder |
| 4,328,593 A | 5/1982 | Sutter et al. |

(Continued)

FOREIGN PATENT DOCUMENTS

DE        2041929        8/1970

(Continued)

OTHER PUBLICATIONS

Biomet Orthopedics, Inc., Introducing the Copeland Humeral Resurfacing Head, 2001.

(Continued)

*Primary Examiner*—Eduardo C Robert
*Assistant Examiner*—David Comstock

(57) ABSTRACT

An instrument for use in removal of a prosthetic implant for use performing arthroplasty is provided. The instrument includes a body and a first member. The first member is operably associated with the body. The first member has a contact portion for engagement with the implant at a first position. The instrument also includes a second member operably associated with the body. The second member is moveable with respect to the first member and the second member has a contact portion for engagement with the implant at a second position, spaced from the first position.

12 Claims, 22 Drawing Sheets

U.S. PATENT DOCUMENTS

| | | | |
|---|---|---|---|
| 4,332,036 A | 6/1982 | Sutter et al. |
| 4,335,429 A | 6/1982 | Kawakatsu |
| 4,355,429 A | 10/1982 | Mittelmeier et al. |
| 4,432,358 A | 2/1984 | Fixel |
| 4,441,492 A | 4/1984 | Rydell et al. |
| 4,550,450 A | 11/1985 | Kinnett |
| 4,601,289 A | 7/1986 | Chiarizzio et al. |
| 4,714,471 A | 12/1987 | Grundei |
| 4,722,330 A | 2/1988 | Russell et al. |
| 4,752,296 A | 6/1988 | Buechel et al. |
| 4,787,378 A | 11/1988 | Sodhi |
| 4,795,473 A | 1/1989 | Grimes |
| 4,801,289 A | 1/1989 | Sugimoto et al. |
| 4,805,607 A | 2/1989 | Engelhardt et al. |
| 4,846,841 A | 7/1989 | Oh |
| 4,865,605 A | 9/1989 | Dines et al. |
| 4,865,609 A | 9/1989 | Roche |
| 4,893,619 A | 1/1990 | Dale et al. |
| 4,919,669 A | 4/1990 | Lannelongue |
| 4,987,904 A | 1/1991 | Wilson |
| 5,064,427 A | 11/1991 | Burkinshaw |
| 5,070,623 A | 12/1991 | Barnes |
| 5,108,396 A | 4/1992 | Lackey et al. |
| 5,116,339 A | 5/1992 | Glock |
| 5,141,520 A | 8/1992 | Goble et al. |
| 5,226,915 A | 7/1993 | Bertin |
| 5,250,051 A * | 10/1993 | Maryan ............... 606/91 |
| 5,258,033 A | 11/1993 | Lawes et al. |
| 5,282,865 A | 2/1994 | Dong |
| 5,358,525 A | 10/1994 | Fox et al. |
| 5,423,827 A | 6/1995 | Mumme et al. |
| 5,423,867 A | 6/1995 | Poore et al. |
| 5,454,816 A | 10/1995 | Ashby |
| 5,470,336 A | 11/1995 | Ling et al. |
| 5,476,467 A | 12/1995 | Benoist |
| 5,486,178 A | 1/1996 | Hodge |
| 5,490,852 A | 2/1996 | Azer et al. |
| 5,507,817 A | 4/1996 | Craig et al. |
| 5,540,696 A | 7/1996 | Booth et al. |
| 5,549,704 A | 8/1996 | Sutter |
| 5,569,263 A | 10/1996 | Hein |
| 5,662,476 A | 9/1997 | Ingber et al. |
| 5,683,395 A | 11/1997 | Mikhail |
| 5,690,636 A | 11/1997 | Wildgoose et al. |
| 5,702,460 A | 12/1997 | Carls et al. |
| 5,723,018 A | 3/1998 | Cyprien et al. |
| 5,735,905 A | 4/1998 | Parr |
| 5,769,852 A | 6/1998 | Brangnemark |
| 5,776,194 A | 7/1998 | Mikol et al. |
| 5,776,201 A | 7/1998 | Colleran et al. |
| 5,779,710 A | 7/1998 | Matsen, III |
| 5,800,437 A | 9/1998 | Gustilo et al. |
| 5,800,557 A | 9/1998 | Elhami |
| 5,830,216 A | 11/1998 | Insall et al. |
| 5,893,850 A | 4/1999 | Cachia |
| 5,957,926 A | 9/1999 | Masini |
| 6,013,104 A | 1/2000 | Kampner |
| 6,045,582 A | 4/2000 | Prybyla |
| 6,063,124 A | 5/2000 | Amstutz |
| 6,071,311 A | 6/2000 | O'Neil et al. |
| 6,102,916 A | 8/2000 | Masini |
| 6,110,200 A | 8/2000 | Hinnenkamp |
| 6,127,596 A | 10/2000 | Brown et al. |
| 6,129,764 A | 10/2000 | Servidio |
| 6,132,469 A | 10/2000 | Schroeder |
| 6,156,069 A | 12/2000 | Amstutz |
| 6,168,628 B1 | 1/2001 | Huebner |
| 6,187,012 B1 | 2/2001 | Masini |
| 6,200,319 B1 | 3/2001 | Storer et al. |
| 6,206,884 B1 | 3/2001 | Masini |
| 6,283,999 B1 | 9/2001 | Rockwood, Jr. |
| 6,319,104 B1 | 11/2001 | Emter |
| 6,334,874 B1 | 1/2002 | Tornier et al. |
| 6,364,910 B1 | 4/2002 | Shultz et al. |
| 6,368,353 B1 | 4/2002 | Arcand |
| 6,508,841 B2 | 1/2003 | Martin et al. |
| 6,554,865 B2 | 4/2003 | Grusin et al. |
| 6,709,439 B2 | 3/2004 | Rogers et al. |
| 6,740,120 B1 | 5/2004 | Grimes |
| 6,755,865 B2 | 6/2004 | Tarabishy |
| 6,783,549 B1 | 8/2004 | Stone et al. |
| 6,942,699 B2 | 9/2005 | Stone et al. |
| 6,979,299 B2 | 12/2005 | Peabody et al. |
| 7,097,397 B2 | 8/2006 | Keightley |
| 2001/0009970 A1 | 7/2001 | Chornenky et al. |
| 2001/0037152 A1 | 11/2001 | Rockwood, Jr. |
| 2001/0047210 A1 | 11/2001 | Wolf |
| 2002/0016634 A1 | 2/2002 | Maroney et al. |
| 2002/0099381 A1 | 7/2002 | Maroney et al. |
| 2002/0099445 A1 | 7/2002 | Maroney et al. |
| 2002/0183849 A1 | 12/2002 | Grusin et al. |
| 2003/0018341 A1 * | 1/2003 | Deloge et al. ............... 606/98 |
| 2003/0114859 A1 | 6/2003 | Grusin et al. |
| 2003/0163202 A1 | 8/2003 | Lakin |
| 2004/0122521 A1 | 6/2004 | Lee et al. |
| 2004/0193277 A1 | 9/2004 | Long et al. |
| 2004/0193278 A1 | 9/2004 | Maroney et al. |
| 2005/0065612 A1 | 3/2005 | Winslow |

FOREIGN PATENT DOCUMENTS

| | | |
|---|---|---|
| DE | 42 28 710 A1 | 3/1993 |
| DE | 04 20 217 C2 | 2/1995 |
| DE | 102 33 204 A1 | 1/2004 |
| EP | 0845250 A2 | 11/1997 |
| EP | 0 888 752 B1 | 7/1998 |
| EP | 0903128 A1 | 9/1998 |
| EP | 1 064 890 B1 | 6/2000 |
| EP | 1 228 739 A3 | 1/2002 |
| EP | 01 288 739 A2 | 1/2002 |
| EP | 1 518 519 | 3/2005 |
| FR | 2418664 | 3/1978 |
| FR | 2 578 739 | 3/1985 |
| FR | 2 737 107 | 7/1995 |
| GB | 764600 | 12/1956 |
| GB | 2 259 253 A | 3/1993 |
| WO | WO 94/15551 | 7/1994 |
| WO | WO 95/22302 | 8/1995 |
| WO | WO 98/07393 | 2/1998 |
| WO | WO 99/37254 | 7/1999 |
| WO | 01/13823 A2 | 3/2001 |
| WO | 01/13823 A3 | 3/2001 |
| WO | WO 02/17822 A1 | 3/2002 |

OTHER PUBLICATIONS

Biomet Merck, Ltd., Copeland Surface Replacement Shoulder Arthroplasty, (date unknown).

Endotec, Inc. Buechel-Pappas, Resurfacing Shoulder System Surgical Procedure by Frederick F. Buechel, M.D. 2001.

Biomet Orthopedics, Inc., Copeland Humeral Resurfacing Head (date unknown).

European Search Report for EPO App No. 04251871.2-1526, Sep. 8, 2004, 3 Pages.

European Search Report for EPO App No. 05251328.0-2310, Jul. 21, 2005, 4 Pages.

European Search Report for APO App No. 04251913.2, Dated Dec. 5, 2005.

Biomet Orthopedics, Inc., Copeland Humeral Resurfacing Head, Date Unknown, 12 pages, Mostly Illegible.

Biomet Brochure (Engineering Drawings Submitted Jul. 22, 1997).

Depuy Orthopaedics, Inc., Introducing the Copeland Humeral Head, 2000, 6 pages, 3.5M0406, 0612-03-050 (Rev. 3), USA.

Depuy Orthopaedics, Inc., Moreland Cemented Hip Revision Instrumentation, pp. 3 and 12 (12 Pages Total), 2.3M500, 0602-28-000 (Rev. 6), USA, 1995.

Depuy Orthopaedics, Inc., Moreland Cementless Hip Revision Instrumentation, pp. 9, 10 and 11 (12 Pages Total), USA 1998.

Smith & Nephew, Inc., Orthopaedic Catalog, pp. 4 and 5 (25 Pages Total), Miscellaneous Instrumentation (Entire Catalog), Prepared Oct. 16, 2003, USA.

Depuy Ace, Engineering Drawings, Title: Articulated Tension Device Outline Drawings—Large Fragment System, P/N. 13710-010, Dec. 11, 1998 (Rev. C), USA.

Depuy Orthopaedics, Inc., Global Advantage CTA Humeral Head, 2000, 6 Pages, 3.5M0406, 0612-03-050 (Rev 3), USA.

\* cited by examiner

SURFACE REPLACEMENT EXTRACTOR DEVICE AND ASSOCIATED METHOD

CROSS-REFERENCE TO RELATED APPLICATIONS

Cross reference is made to the following applications: U.S. patent application Ser. No. 10/403,707 filed Mar. 31, 2003, entitled "ARTHROPLASTY SIZING GAUGE", now U.S. Pat. No. 7,527,631 B2, U.S. patent application Ser. No. 10/403,750 filed Mar. 31, 2003, entitled "ARTICULATING SURFACE REPLACEMENT PROSTHESIS", U.S. patent application Ser. No. 10/403,577 filed Mar. 31, 2003, entitled "MODULAR ARTICULATING SURFACE REPLACEMENT PROSTHESIS", U.S. patent application Ser. No. 10/403,710 filed Mar. 31, 2003, entitled "ARTHROPLASTY INSTRUMENT AND ASSOCIATED METHOD", U.S. patent application Ser. No. 10/403,708 filed Mar. 31, 2003, entitled "EXTENDED ARTICULATION ORTHOPAEDIC IMPLANT AND ASSOCIATED METHOD", now U.S. Pat. No. 7,517,364 B2, and U.S. patent application Ser. No. 10/403,364 filed Mar. 31, 2003, entitled ""PROSTHETIC IMPLANT, TRIAL AND ASSOCIATED METHOD", now U.S. Pat. No. 7,338,498 B2, which are incorporated herein by reference in their entities.

TECHNICAL FIELD OF THE INVENTION

The present invention relates generally to the field of orthopaedics, and more particularly, to an instrument for use in arthroplasty.

BACKGROUND OF THE INVENTION

The present invention relates to implantable articles and methods of for implanting such articles. More particularly the invention relates to a bone prosthesis, prosthesis trial, instrument and method for implanting the same.

There are known to exist many designs for and methods for implanting implantable articles, such as bone prostheses. Such bone prostheses include components of artificial joints, such as elbows, hips, knees and shoulders.

One such implantable prosthesis is a shoulder prosthesis. During the life time of a patient, it may be necessary to perform a total shoulder replacement procedure on a patient as a result of, for example, disease or trauma, for example disease from osteoarthritis or rheumatoid arthritis. Currently, most implantable shoulder prostheses are total shoulder prostheses. In a total shoulder replacement procedure, a humeral component having a head portion is utilized to replace the natural head portion of the upper arm bone or humerus. The humeral component typically has an elongated intermedullary stem, which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

With the average age of patients requiring shoulder arthroplasty surgery decreasing, orthopaedic implant manufacturers are developing "bone-sparing" implants for the initial treatment of the degenerative arthritis. While bone-sparing implants for the treatment hip and knee arthroplasty are becoming quite common, bone-sparing shoulder arthroplasty techniques and prostheses are also being developed.

Shoulder surface replacement prostheses are being developed to replace the articulating surface of the proximal humerus with a minimal bone resection and minimal disruption of the metaphysis and the diaphysis. Current designs use a semi-spherical articular dome with a small stem for rotational stability. The under surface of the articular head is also semi-spherical and meets with a spherically machined humeral.

Typically, however, arthritis of the gleno-humeral joint causes flattening of the humeral head with a large medial osteophyte. The flat humeral head can cause voids in the bone under the prosthesis resulting in limited contact between the prosthesis and the resected bone and may limit the load transfer capability between the prosthesis and the humerus. During a surface replacement procedure, it may be necessary to remove the initial implant once seated because of incorrect sizing. The correct sizing may be determined, for example, during the trialing of an implant. Prior art attempts at removing the implant have resulted in the damage of the surrounding bone during the removal of the implant.

Alternatively, a surface replacement implant may need to be revised where damage has occurred to surface replacement implant or to the corresponding glenoid component. During such a replacement procedure the initial implant will need to be extracted. Extraction of the initial implant may be made more difficult if the initial implant includes a porous coating to promote bony in-growth. The bony in-growth of the surface implant stem may make the removal of the surface replacement prosthesis extremely difficult.

Due to the nature of the progression of the aging or disease of the joint caused by, for example, osteoarthritis, or due to prosthesis wear it may be necessary to revise or replace the surface replacement prosthesis with a total joint prosthesis. The surface replacement prosthesis must be removed from the bone so that bone may be resected.

Prior art procedures for the removal of the surface replacement prostheses have been limited to the use of an osteotome and a mallet to wedge the implant from under the outer lip of the implant and free the implant from the bone underneath the implant.

The removal of the implant from the bone using an osteotome and a wedge is wrought with many problems including damage to the bone around the implant and generally difficulty in removal of the implant. The present invention is intended to resolve at least some of the aforementioned problems.

SUMMARY OF THE INVENTION

According to the present invention, a device is provided for use to extract a surface replacement implant in a singular axial motion without damaging the bone interoperatively. The devise may be used to extract a surface implant for a revision procedure.

Such a device may include a surface replacement implant extractor device that may, for example, include lever arms that are designed to fit around a range of implant sizes and clamp underneath the lip of the cup with a (baseball) type grip. For example, the extractor devise may include a first lever arm with two fingers and a second lever arm with a single finger.

The extractor device may include a set of lever arms that are tightened with a simple rotating handle.

The extractor device include a handle having a shaft that the surgeon may utilize with a common slotted mallet to strike the extractor device underneath the handle along the shaft to assist removal of the implant.

According to the present invention, the extractor device may be able to clamp around surface replacement implants with multiple diameters and head heights underneath the cupped lips firmly with a turnbuckle activated by a two finger and thumb baseball type grip with a simple turn of the handle. The device furthermore provides for extracting the implant from the long bone in an axial motion with one motion of a slotted mallet without damaging the bone surrounding the implant.

According to one embodiment of the present invention, there is provided an instrument for use in removal of a prosthetic implant for use in performing arthroplasty. The instrument includes a body and a first member. The first member is operably associated with the body. The first member has a contact portion for engagement with the implant at a first position. The instrument also includes a second member operably associated with the body. The second member is moveable with respect to the first member and the second member has a contact portion for engagement with the implant at a second position, spaced from the first position.

According to another embodiment of the present invention there is provided an instrument for use in removal of a prosthetic implant having a hollow generally hemispherical portion having a peripheral rim. The implant is used for performing arthroplasty. The instrument includes a body and a first member. The first member is operably associated with the body. The first member has a contact portion for engagement with the rim of the implant at a first position. The instrument also includes a second member operably associated with the body. The second member is moveable with respect to the first member. The second member has a contact portion for engagement with the implant at a second position, spaced from the first position.

According to still another embodiment of the present invention there is provided a kit for use in performing arthroplasty. The kit includes an implant and an instrument. The instrument is for use in removal of a prosthetic implant for use performing arthroplasty. The instrument includes a body and a first member operably associated with the body. The first member has a contact portion for engagement with the implant at a first position. The instrument also includes a second member operably associated with the body. The second member is moveable with respect to the first member. The second member includes a contact portion for engagement with the implant at a second position, spaced from the first position.

According to a further embodiment of the present invention, there is provided a method for removing a surface replacement implant from a long bone. The method includes the step of providing an instrument having a body, a first member and a second member, the first member being operably associated with the body and including a contact portion for engagement with the implant at a first position, the second member being operably associated with the body and being moveable with respect to the first member, the second member including a contact portion for engagement with the implant at a second position, spaced from the first position. The method also includes the steps of separating the first contact portion from the second contact portion and placing the instrument into alignment with the implant. The method also includes the steps of advancing the first contact portion toward the second contact portion and retracting the instrument and implant from the long bone.

Technical advantages of the present invention include the ability of the invention to remove an implant without damaging the surrounding bone. For example, according to one aspect of the present invention an instrument is provided that has a first member for contact with a portion of the bone and a second member for contact with a portion of the bone. The instrument is designed so that the implant that can be removed in a direction reverse to that of the implanting direction. Thus, the present invention provides for removing the implant without damaging the surrounding bone.

The technical advantages of the present inventions, further include the ability to remove the implant when there is extensive bony in-growth of the bone into the implant. For example, according to one aspect of the present invention an instrument is provided which provides a firm grip of the implant and sufficient strength and rigidity to remove the implant without damaging the instrument or the implant. Thus the present invention provides for removal of the implant when there is excessive bony in-growth.

The technical advantages of the present invention also include the ability to remove different sizes of implants with one tool. For example, according to one aspect of the present invention an instrument includes a first member and a second member with the first member being movable with respect to the second member to accommodate several sizes with one tool. Thus the present invention provides for the removal of different size implants with one tool.

Another technical advantage of the present invention includes the ability of the instrument to be used with one hand. For example, according to another aspect of the present invention the first and second members are lockably engaged with the implant and a distal handle is provided. Thus the present invention provides for the use of the tool with one hand.

Another technical advantage of the present invention is the ability of the instrument to be used with a mallet. For example, according to one aspect of the present invention the instrument includes a surface for receiving strikes with a mallet. Further the instrument may include a cylindrical shaft portion for engagement with a slotted mallet. Thus the present invention provides for an instrument that may be used with a mallet.

Technical advantages of the present inventions further include the ability to permit the removal of the initial implant to perform revisions of the stem implant. For example, according to one aspect of the present invention, the instrument includes a first member and a second member for engaging the implant and to permit the removal of an implant in the axial direction. Thus the present invention provides for the removal of the initial implant to perform revisions to the stem implant.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Figure 1:
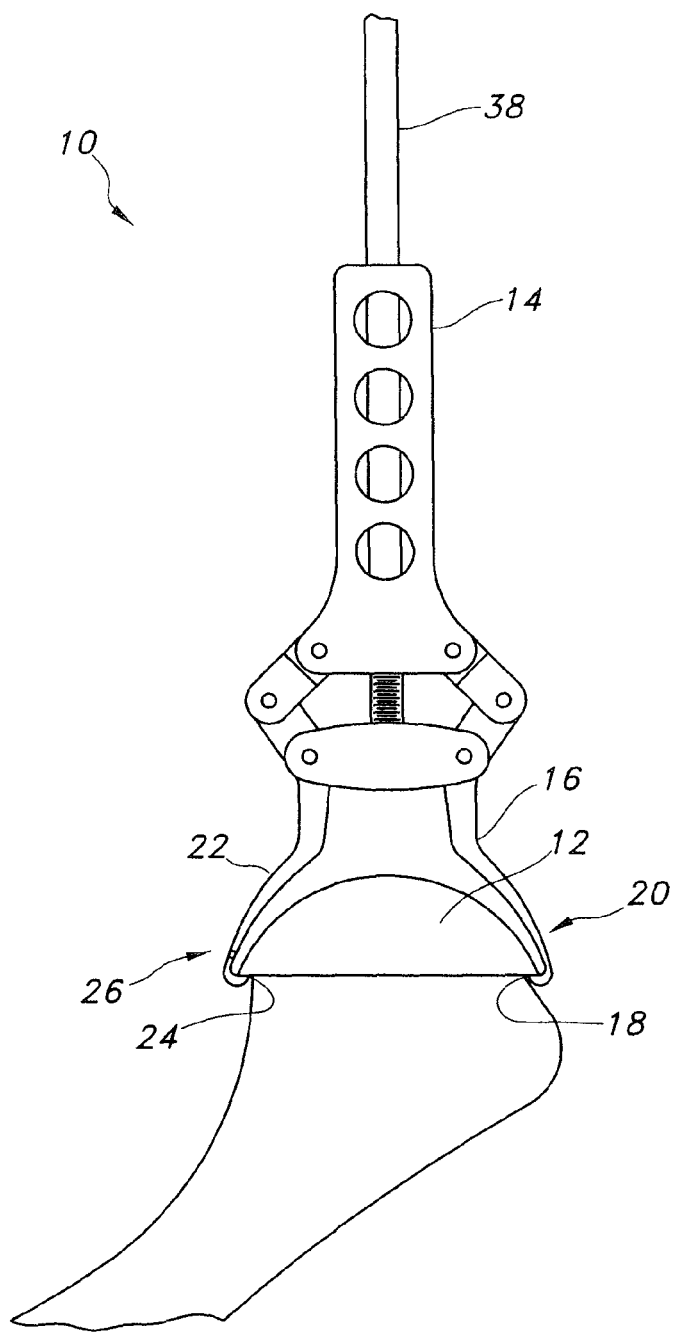
FIG. 1 is a partial plan view of the extractor in accordance with an embodiment of the present invention in position in engagement with a prosthesis to be extracted.

Embodiments of the present invention and the advantages thereof are best understood by referring to the following descriptions and drawings, wherein like numerals are used for like and corresponding parts of the drawings According to the present invention and referring now to FIG. 1, an instrument 10 is shown for use in removal of a prosthesis implant, for example, conservative humeral implant 12 for use in performing arthoplasty. The instrument 10 includes a body 14 and a first member 16. The first member 16 is operably associated with the body 14. The first member 16 includes a contact portion 18 for engagement with the implant 12 at the first position 20.

The instrument 10 further includes a second member 22. The second member 22 is operably associated with the body 14. The second member 22 is movable to respect to the first member 16. The second member 22 includes a contact portion 24 for engaged with the implant 12 at a second position 26 spaced from the first position 20.

Figure 2:
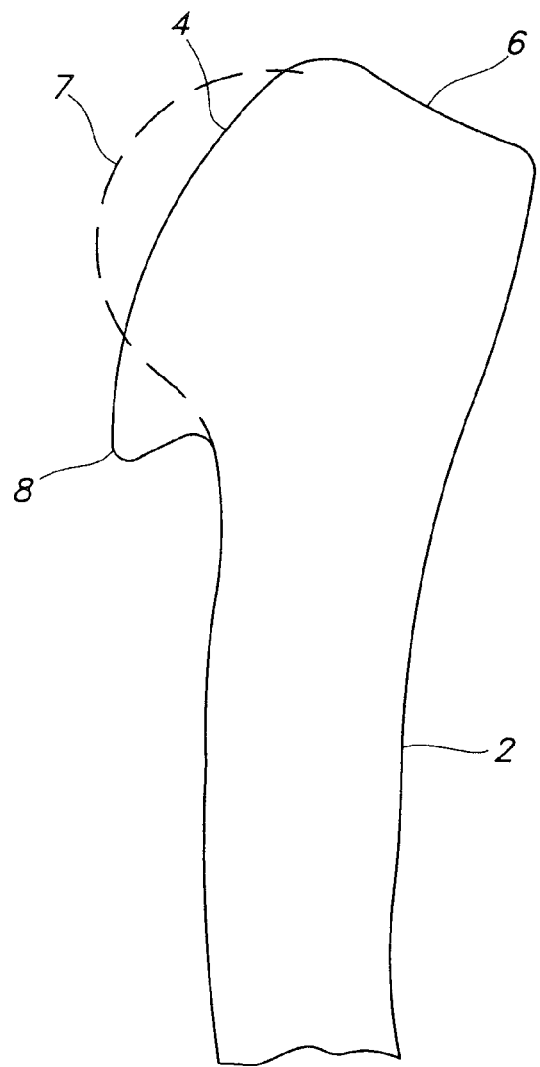
FIG. 2 is a plan view of a diseased humerus.

Referring now to FIG. 2, a diseased humerus is shown. The diseased humerus 2 includes a greater tubercle 6 for located in the head 4 of the humerus 2. The greater tubercle 6 is worn or flattened from its original position 7 as shown in phantom. The lesser tubercle 8 is also shown.

Figure 3:
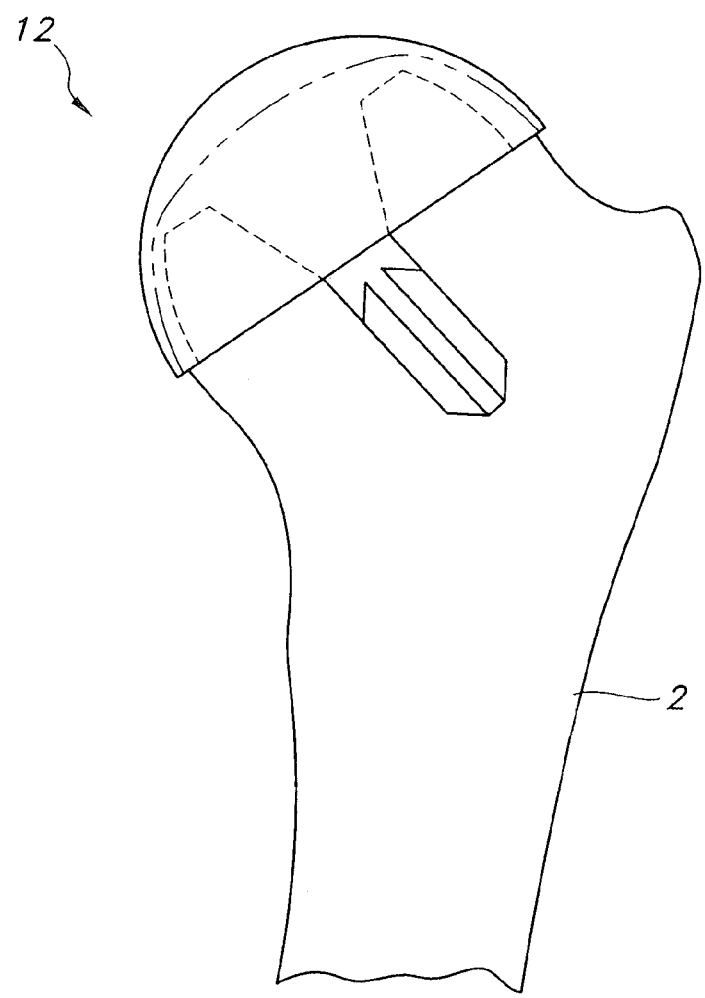
FIG. 3 is a plan view of a partially in cross section of a conservative shoulder prosthesis that may be extracted with the extractor of the present invention implanted into the diseased humerus of FIG. 2.

Referring now to FIG. 3, the prosthesis or implant 12 is shown positioned on humerus 2.

Figure 4:
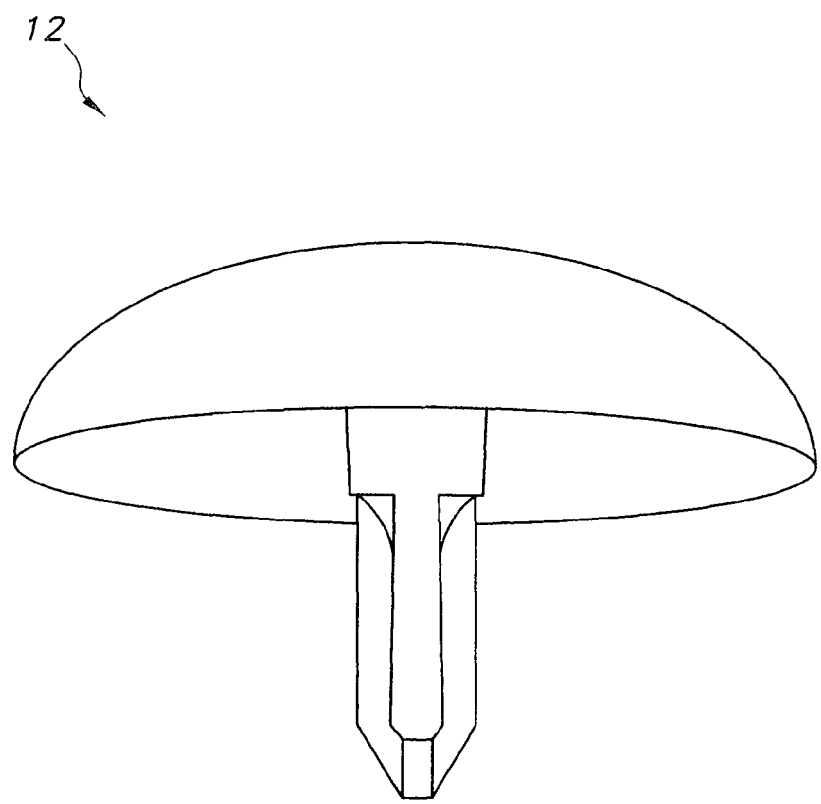
FIG. 4 is a perspective view of the conservative shoulder prosthesis of FIG. 3.

Referring now to FIG. 4, the prosthesis 12 is shown in greater detail.

Figure 5:
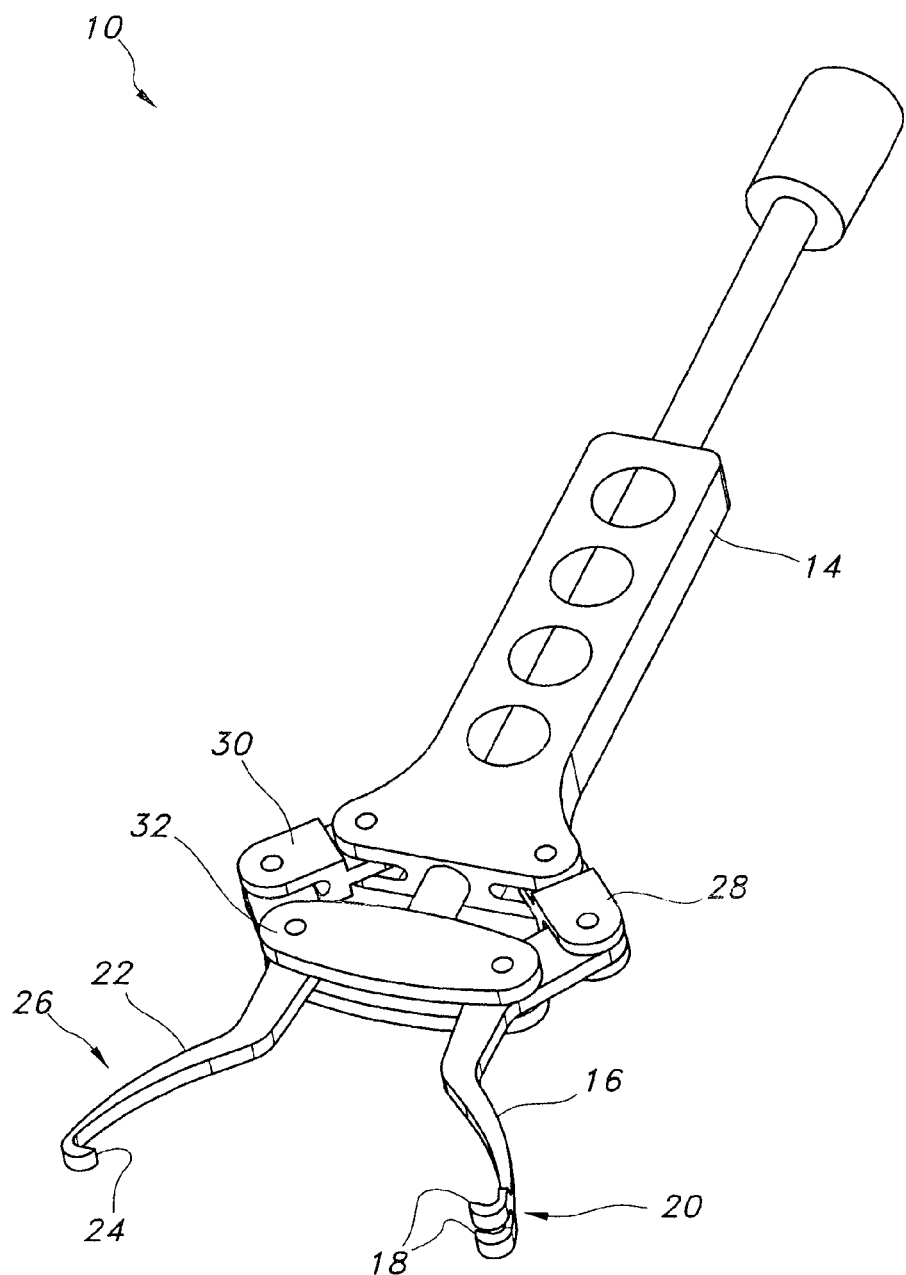
FIG. 5 is a perspective view of the extractor of FIG. 1 in accordance with an embodiment of the present invention.

Referring now to FIG. 5, the instrument 10 is shown in greater detail. Preferably is shown in FIG. 5 the first member 16 is movable in respect to the body 14 and the second member 22. The first member 16 may be movable in any way capable to perform its function under the present invention. The first and second members may as shown in FIG. 5, be such that the first member 16 and/or second member 22 may be pivotally attached to the body 14.

Figure 15:
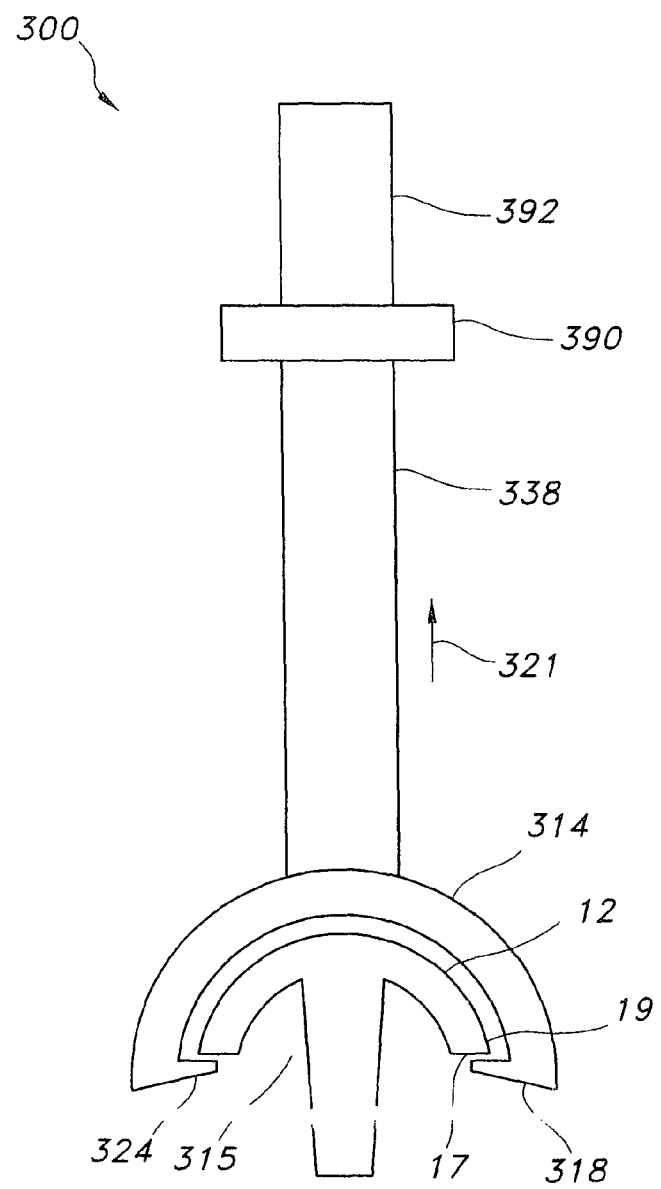
FIG. 15 is a plan view of another embodiment of the present invention in the form of a pliable extractor for extracting a conservative humeral shoulder prosthesis.

It should be appreciated that the first member 16 and the second member 22 may be directly pivotally attached to body 14. It should be appreciated, as is shown in FIG. 15 that the first member 16 and the second member 22 may be indirectly attached to the body 14. For example, and is shown in FIG. 5, the first member 16 may be pivotally attached to a first linking member 28 which in turn is pivotally linked to body 14. Similarly the second member 22 may include a second linking member 30 which may be positioned between the second member 22 and the body 14 to provide pivotal linking of the second member 22 to the body 14.

Figure 6:
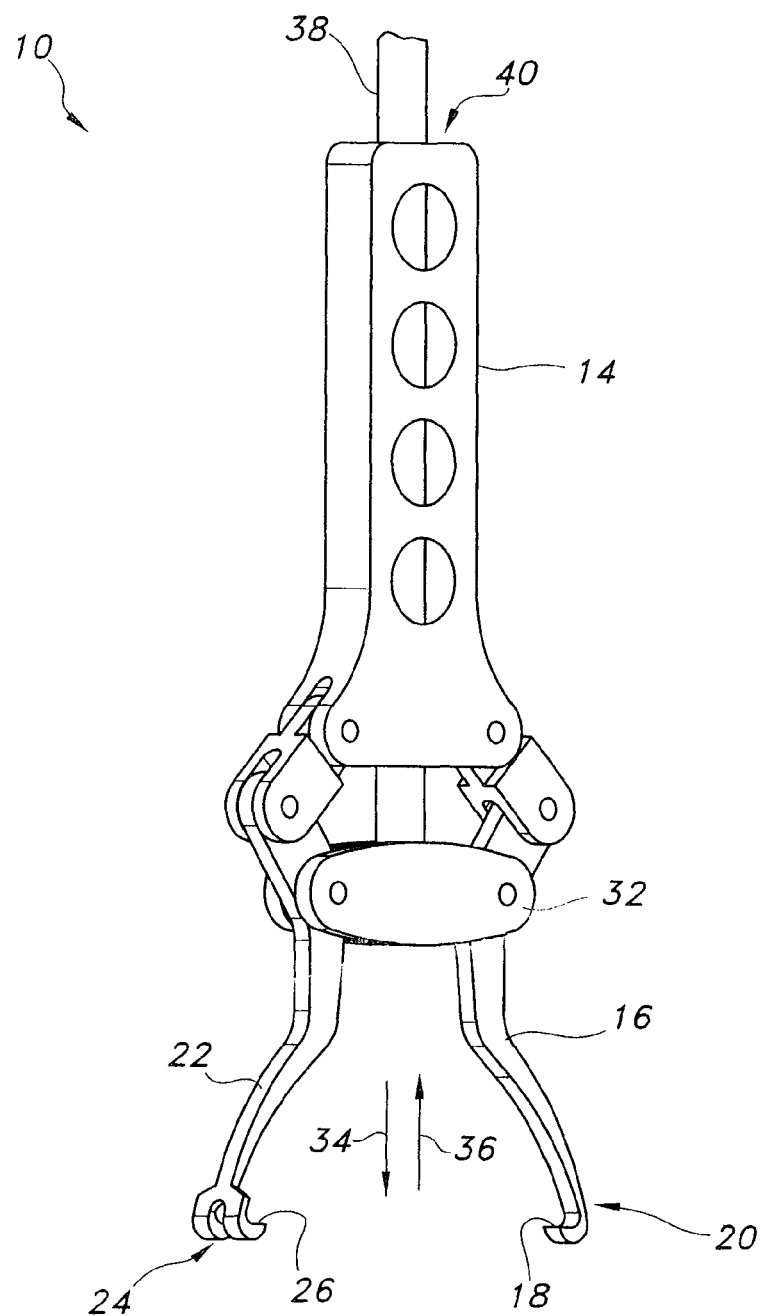
FIG. 6 is a partial perspective view of the extractor of FIG. 1 showing the expansion mechanism in greater detail.

Referring now to FIG. 6, the instrument 10 is shown in greater detail. As shown in FIG. 6 the instrument 10 may include a third linking member 32 connecting the second member 22 to the first member 16. The third linking member 32 may be movable in direction of arrows 34 and 36 by, for example, threaded shaft 38 threadably secured in longitudinal opening 40 formed in the body 14.

Figure 7:
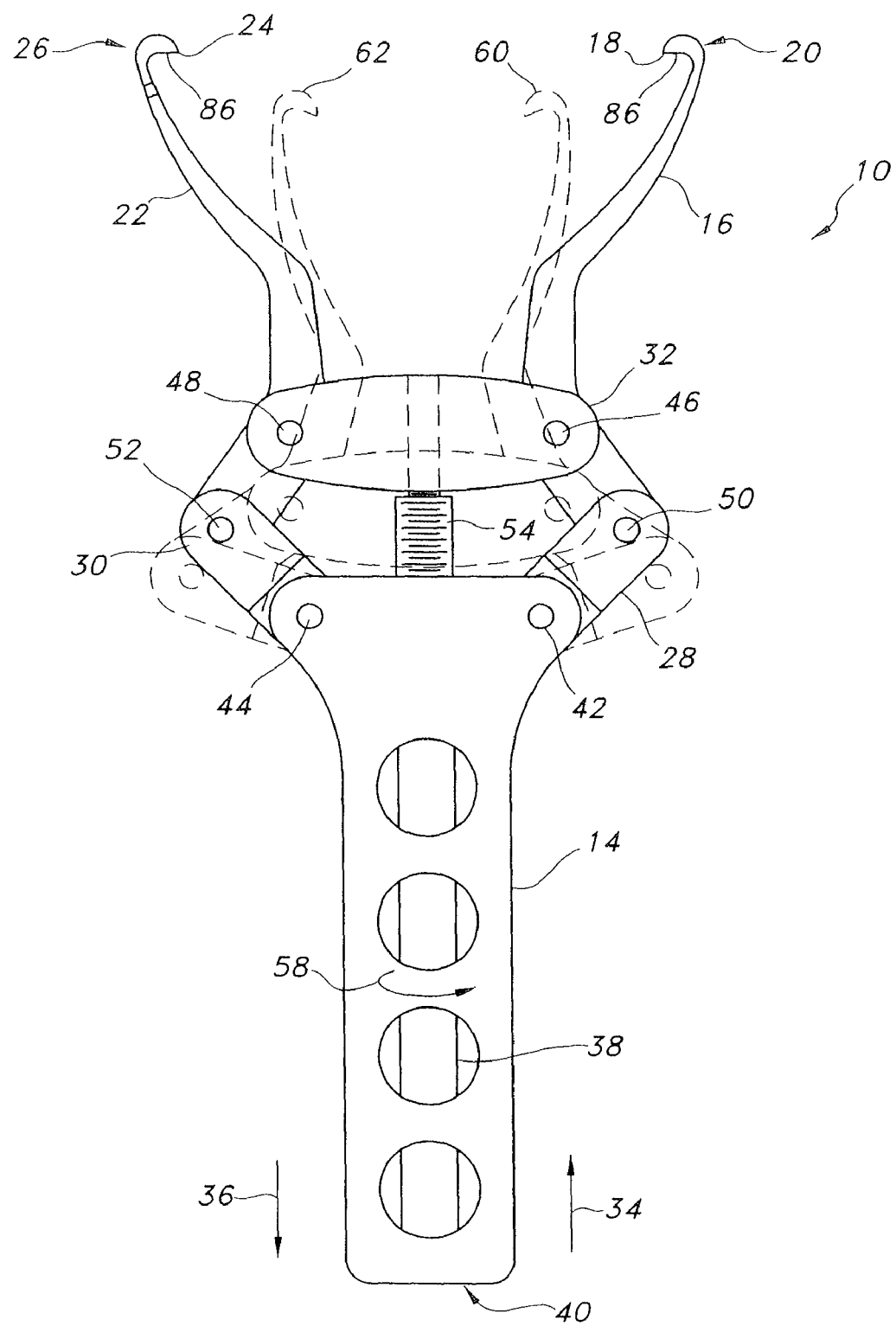
FIG. 7 is a partial plan view of the extractor of FIG. 1 showing the expansion mechanism in yet greater detail.

Referring now to FIG. 7, the instrument 10 is shown in greater shown. As shown in FIG. 7 the first linking member 28 pivotally rotates about first body pin 42 while second linking member 30 pivots about second body pin 44.

The first member 16 rotates relative third linking member 32 about third member first pin 46 while the second member 22 rotates about third linking member 32 around third linking member second pin 48. The first member 16 is pivotally connected to the first linking member 28 at first linking member pin 50 while the second linking member 30 is pivotally connected to the second member 22 at second linking member pin 52.

As shown in FIG. 7, the shaft 38 may include a turnbuckle 54 located at first end 56 of the shaft 38. The turnbuckle 54 communicates with the third linking member 32 and with the body 14 to more the third linking member toward and away from the body 14 as the shaft 38 is rotated.

For example, and is shown in FIG. 7, if the shaft 38 is rotated in the first direction 58 the third linking member 32 is drawn toward the body 14 causing the first contact portion 18 of the first member 16 to move from first position 20 to position 60 as shown in phantom. Similarly, as shaft 38 is rotated into the direction of arrow 58 the second contact portion 24 of the second member 22 is moved from second position 26 to position 62 (also shown in phantom).

Figure 7A:
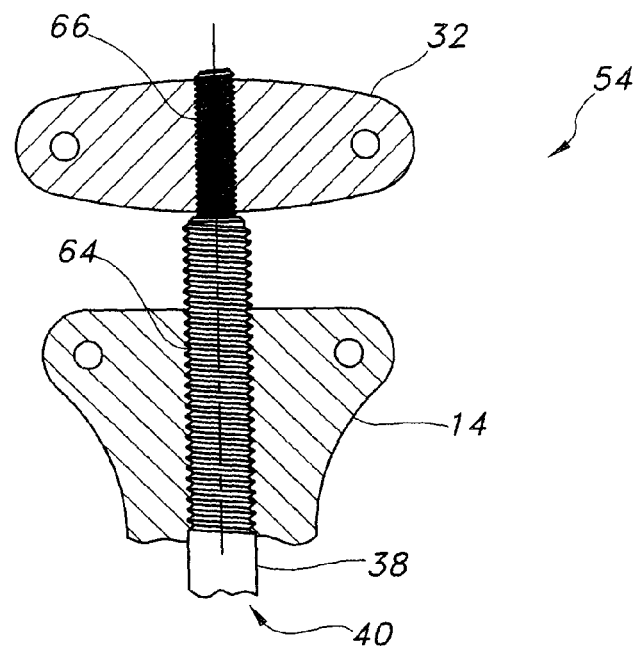
FIG. 7A is a partial plan view, partially in cross section, of the extractor of FIG. 1 showing the turnbuckle mechanism in yet greater detail.

Referring now to FIG. 7A, the turnbuckle 54 is shown in greater detail. As shown in FIG. 7A, the turnbuckle 54 includes a left handed thread portion 64 for cooperation with the body 14 and a right hand threaded portion 66 for cooperation with the third linking member 32. The left handed thread portion 64 and the right handed thread portion 66 may as shown in FIG. 7A be integral with the shaft 38 and may be located near the end of the shaft 38.

Figures 7B, 7C:
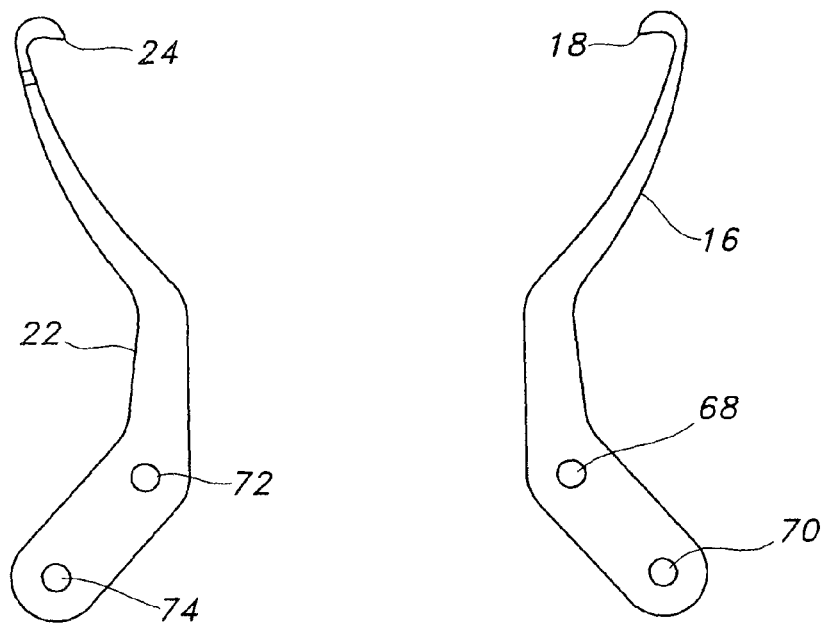
FIG. 7B is a partial plan view of the extractor of FIG. 1 showing the first member in greater detail.
FIG. 7C is a partial plan view of the extractor of FIG. 1 showing the second member in greater detail.

Referring now to FIG. 7B, the first member 16 is shown in greater detail. As shown in FIG. 7B, the first member 16 includes first contact portion 18 extending at a first end of the first member 16 and first pivot hole 68 positioned intermediately on the second member 16. The first pivot hole 68 is designed for cooperation with the third linking member first pin 46 (see FIG. 7). The first member 16 may also include a second pivot hole 70 located on the end opposed to the first contact portion 18. The second pivot hole 70 is for cooperation with the first linking member pin 50 (See FIG. 7).

Referring now to FIG. 7C, the second member 22 is shown in greater detail. The second member 22 is similar to the first member 16 and is, as shown in FIGS. 7B and 7C, symmetrical to the first member 16. The second member 16 includes the first contact portion 24. Intermediate first pivot hole 72 is positioned intermediately on the second member 22. The first pivot hole 72 is for cooperation with the third linking member second pin 48. The second member 22 includes the second pivot hole 74 for cooperation with the second linking member pin 52. The second contact portion 24 may be similar to the first contact portion 18 of the first member 16 or may, as shown in FIGS. 7C and 7D have a forked or split-apart configuration to more stably support and cooperate with the implant 12.

Figure 7D:
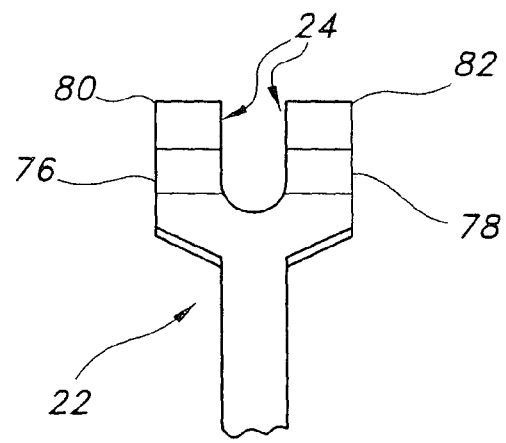
FIG. 7D is a partial plan view of the extractor of FIG. 1 showing the arm of the second member in greater detail.

For example and referring now to FIG. 7D, the contact portion 24 is shown in greater detail as a split-apart or forked contact portion. The second contact portion 24 of the second member 22 may include a first tine 76 and a spaced-apart second tine 78. The first tine 76 defines a first contact portion 80 while the second tine 78 defines a second spaced apart contact portion 82.

While the first contact portion 18 of the first member 16, as shown in FIG. 7D, and the second contact portion 24 of the second member 22 (see FIGS. 7C and 7D) may have any suitable shape, preferably, contact portions 18 and 24 have a pointed or wedge shape.

Figure 7F:
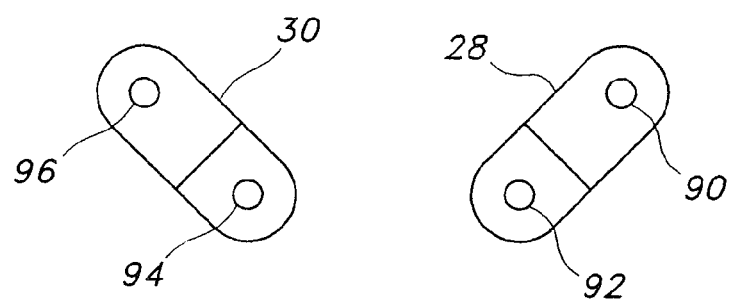
FIG. 7F is a partial plan view of the extractor of FIG. 1 showing the first and second links in greater detail.
Figure 7E:
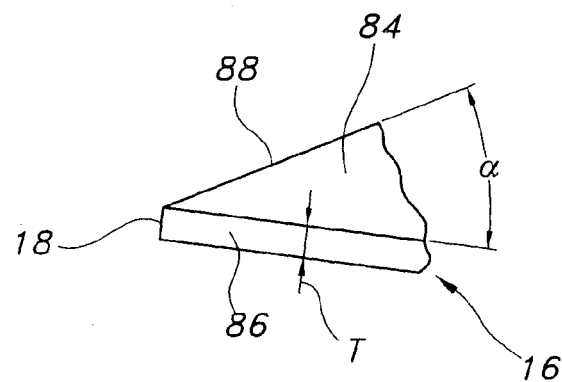
FIG. 7E is a partial plan view of the extractor of FIG. 1 showing the showing the contact portion of the first member in greater detail.

Referring now to FIG. 7E, the contact portion 18 is shown in greater detail. The first contact portion 18 is defined by generally wedge shaped having an angle $\alpha$ and having spaced-apart opposed faces 84. The spaced-apart faces 84 may be separated by a constant distance, for example T. A contact portion 18 may include an inner contact surface 86 and an outer contact surface 88. The inner contact surface 86 and the outer contact surface 88 may be defined by an included angle $\alpha$ there between. The angle $\alpha$ may be, for example 5 to 45 degrees with, for example, about 15 degrees preferred. The inner contact surface 86 may contact the inner lip of the implant to assist in the removal from the humerus.

Referring now to FIG. 7F, the second linking member 30 and the first linking member 28 are shown in greater detail. The first linking member 28 includes a first hole 90 and a spaced-apart second hole 92. The first hole 92 is for cooperation with the first body pin 42 while the second hole 92 is for cooperation with the first linking member pin 50. The second linking member 30 includes a first hole 94 and a spaced-apart second hole 96. The first hole 94 is for cooperation with the second body pin 44 while the second hole 96 is for cooperation with the second linking member pin 52.

The instrument 10 may be made with any suitable, durable material. Preferably the instrument 10 is made of a material that can be sterilized by conventional sterilization techniques such as by autoclaving. The instrument 10 may be made of a metal or a plastic. If made of a metal, the instrument 10, for example, may be made of a cobalt chromium alloy, a titanium alloy, or a stainless steel alloy. The instrument 10 may be made of components that are forged, sand cast, investment cast, or made by other techniques. The components may be machined or manufactured using any suitable techniques.

Figure 8:
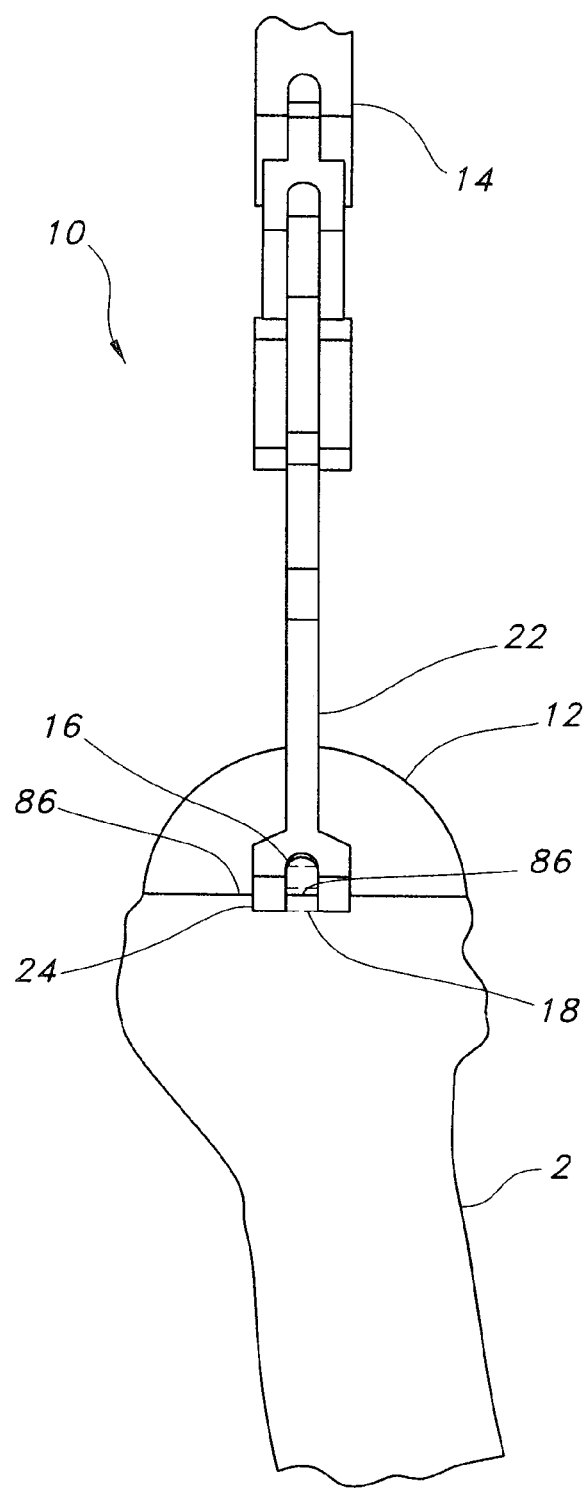
FIG. 8 is a partial plan view of the extractor of FIG. 1 in engagement with a conservative hip prosthesis.

Referring now to FIG. 8, the instrument 10 is shown engaged with prosthesis 12 for the removal of the prosthesis 12 from the humerus 2. Inside surface 86 of the contact portions 18 and 24 of the first member 16 and the second member 22, respectively are shown in engagement with the prosthesis 12.

Figure 9:
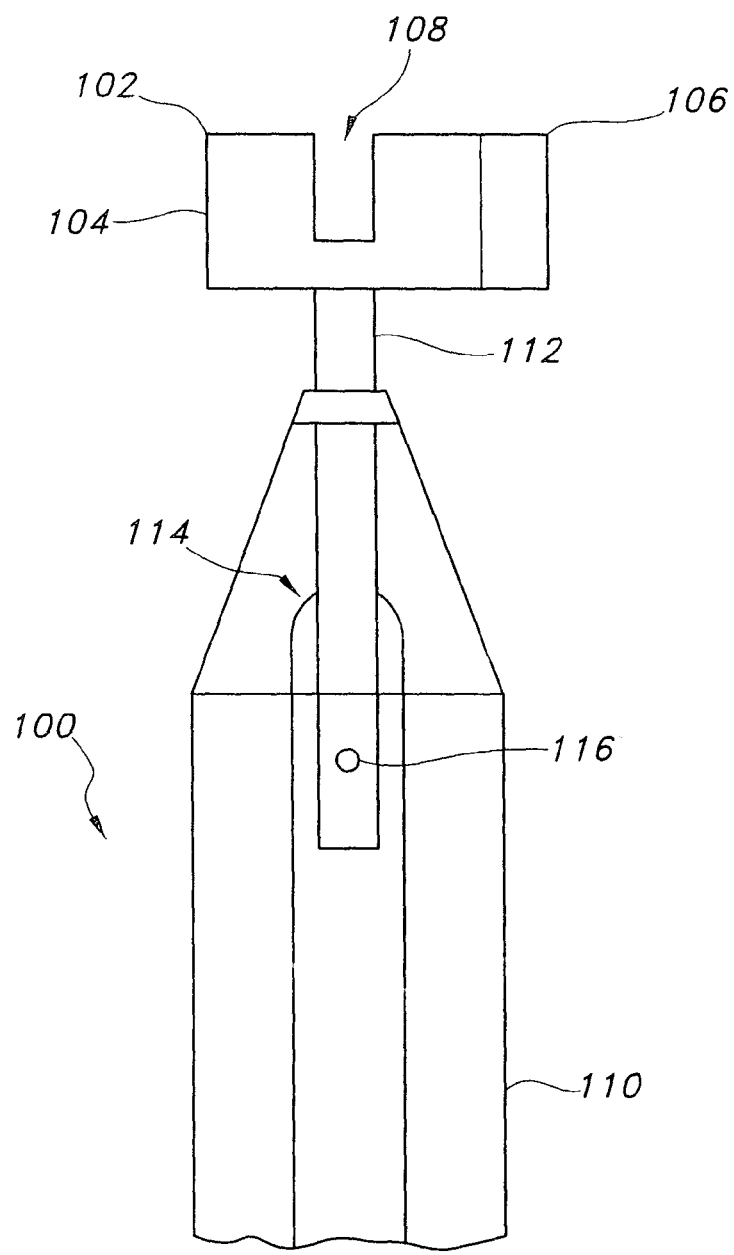
FIG. 9 is a plan view of a hammer for use with the extractor of FIG. 1.

Referring now to FIG. 9, a hammer 100 is shown for use with the instrument 10 of FIGS. 1-8. The hammer 100 includes a head 102 including a hard portion 104 made of, for example, a metal and a soft portion 106 made of, for example, a plastic. The head 102 may include a slot or opening 108 for cooperation with the shaft 38 of the instrument 10 (see FIG. 7). The head 102 may be secured to the handle 110 by any suitable mechanism including for example a stem 112 extending from the head 102. The stem may be connected to the handle through a longitudinal opening 114 in the handle 110 and may be secured to the handle 110 by, for example, a pin 116.

It should be appreciated that alternatively the hammer may be in the form of a slap hammer or a cylindrical member (not shown) that has a central opening which is slidably fitted to the shaft 38 of the instrument 10 and restrained to the instrument at the ends of the shaft 38. The outer periphery of the slap hammer is grabbed by the hand to strike the slap hammer.

The handle 110 may be made of any suitable durable material, for example, a metal, a plastic, or a natural material, for example, wood.

Figure 10:
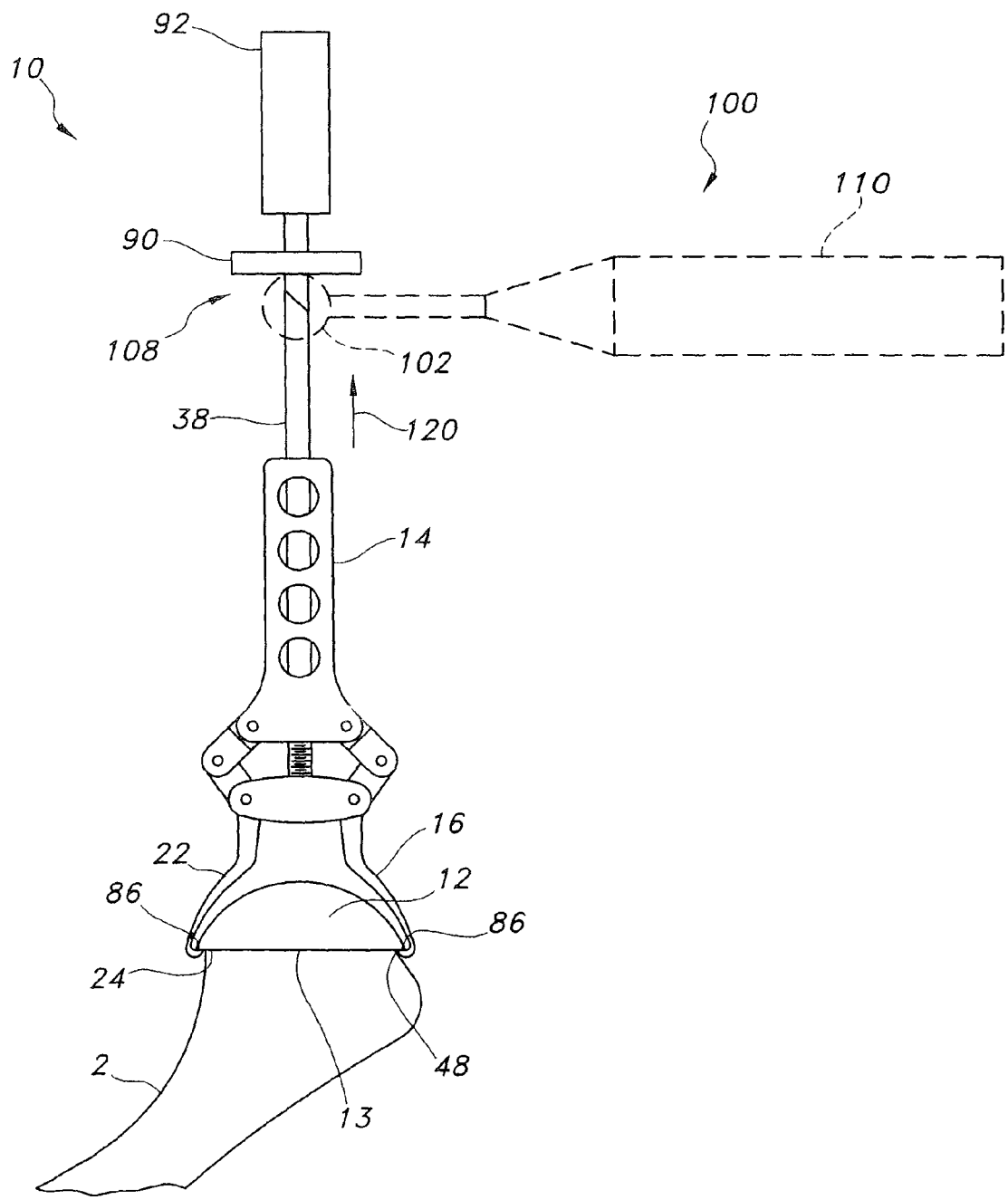
FIG. 10 is a partial plan view of the extractor of FIG. 1 in engagement with a conservative hip prosthesis with the hammer of FIG. 9 in engagement with the extractor.

Referring now to FIG. 10, the hammer 100 is shown in cooperation with the instrument 10. To utilize the instrument 10 to remove the prosthesis or cap 12 from the humerus 2, the instrument 10 is placed over and beyond the cap 12 and first member 16 and second member 22 are pivoted apart to permit the lips 48 and 24 of the first member 16 and the second member 22, respectively, to pass over the cap 12.

The inner lip surfaces 86 of the first member 16 and the second member 22 are then positioned to engage end face 13 of the cap 12. Next the first member 16 and the second member 22 are drawn together to securely in engage the cap 12 by a rotation of the shaft 38.

After the instrument 10 has been secured to the cap 12 the surgeon places the head 102 of the hammer 100 in engagement with the instrument 10 by passing the slot 108 of the head 102 into engagement with the shaft 38 of the instrument 10. By advancing the hammer 100 in the direction of arrow 120, the cylindrical portion of the head 102 of the hammer 100 strikes collar 90 of the instrument 10 secured to an end to the shaft 38. The surgeon may steady the instrument 10 by holding on to the handle 92 of the instrument 10 positioned outwardly from the collar 90. After the cap 12 has been removed from the humerus 2, the handle 92 may be rotated relative to the body 14 on the instrument 10 to release the cap 12 from the instrument 10.

Figure 11:
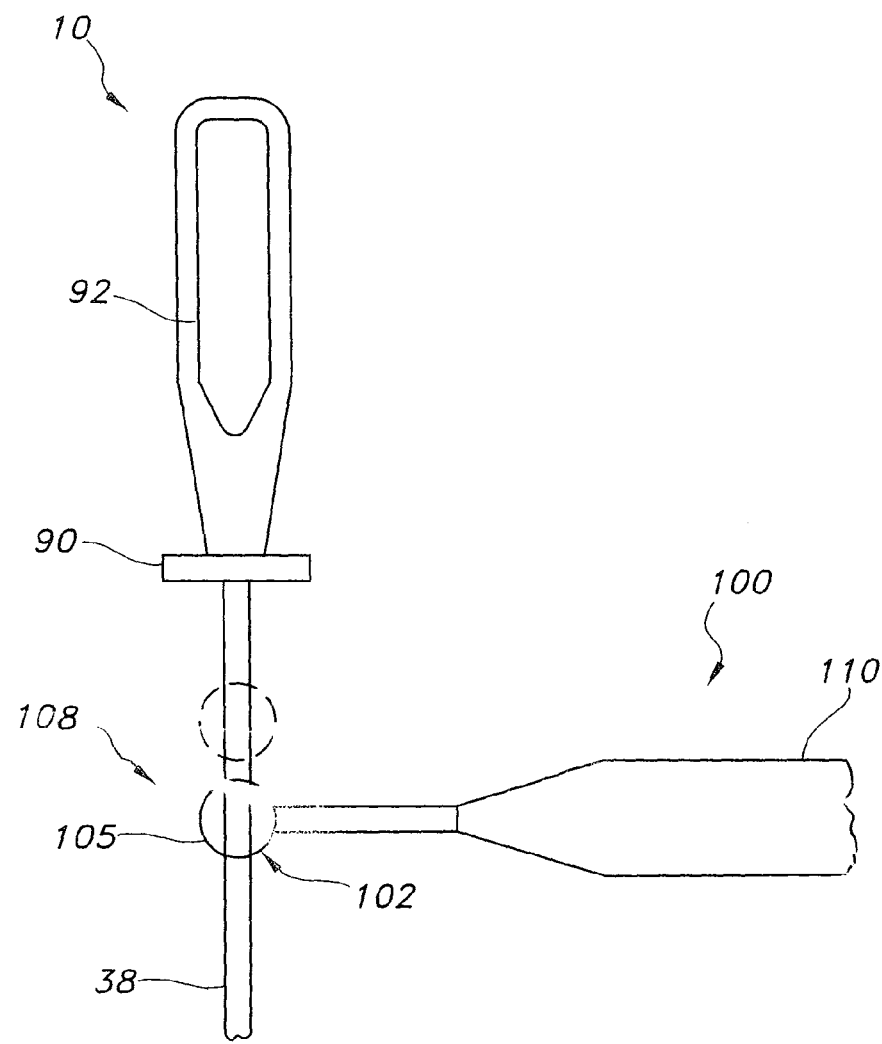
FIG. 11 is a partial plan view of the hammer of FIG. 9 in engagement with the extractor of FIG. 1.

Referring now to FIG. 11, the hammer 100 is shown in greater detail against collar 90 of the instrument 10. The cylindrical collar 90 of the head 102 of the hammer 100 is struck against the instrument 10.

Figure 12:
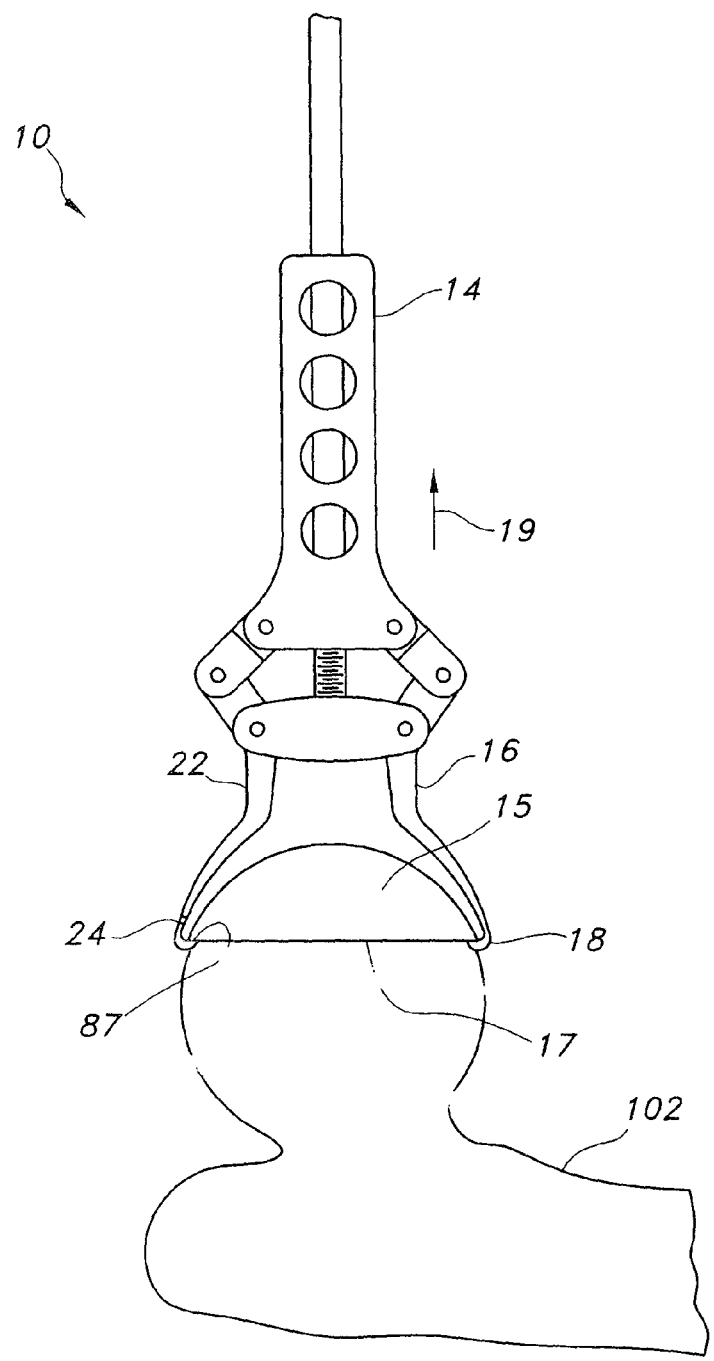
FIG. 12 is a plan view of the extractor of FIG. 1 in engagement with a conservative femoral hip prosthesis.

Referring now to FIG. 12, the instrument 10 is shown for use in femoral implant 15 for use in conservative arthoplasty of femur 102. Femur implant 15 is quite similar to the humeral implant 12 of FIGS. 1-5 expect that femoral implant 15 fits on head 103 of the femur 102 rather than on the head of the humerus 2 of FIGS. 1-5.

When utilized to remove a femoral implant 15, the instrument 10 is used similarly to how it is used to remove a humeral implant 12. For example, and is shown in FIG. 12, the first member 16 and the second member 22 of the instrument 10 are pivoted apart such that the first contact portion 18 and the second contact portion 24 may pass over the femoral implant 15 and lip surface 86 of the first contact portion 18 and the second contact portion 24 engage with outer surface 17 of the femoral implant 15. The instrument 10 with the implant 15 attached thereto, is advanced in the direction of arrow 19 to remove the implant 15 from the femur 102.

Figure 13:
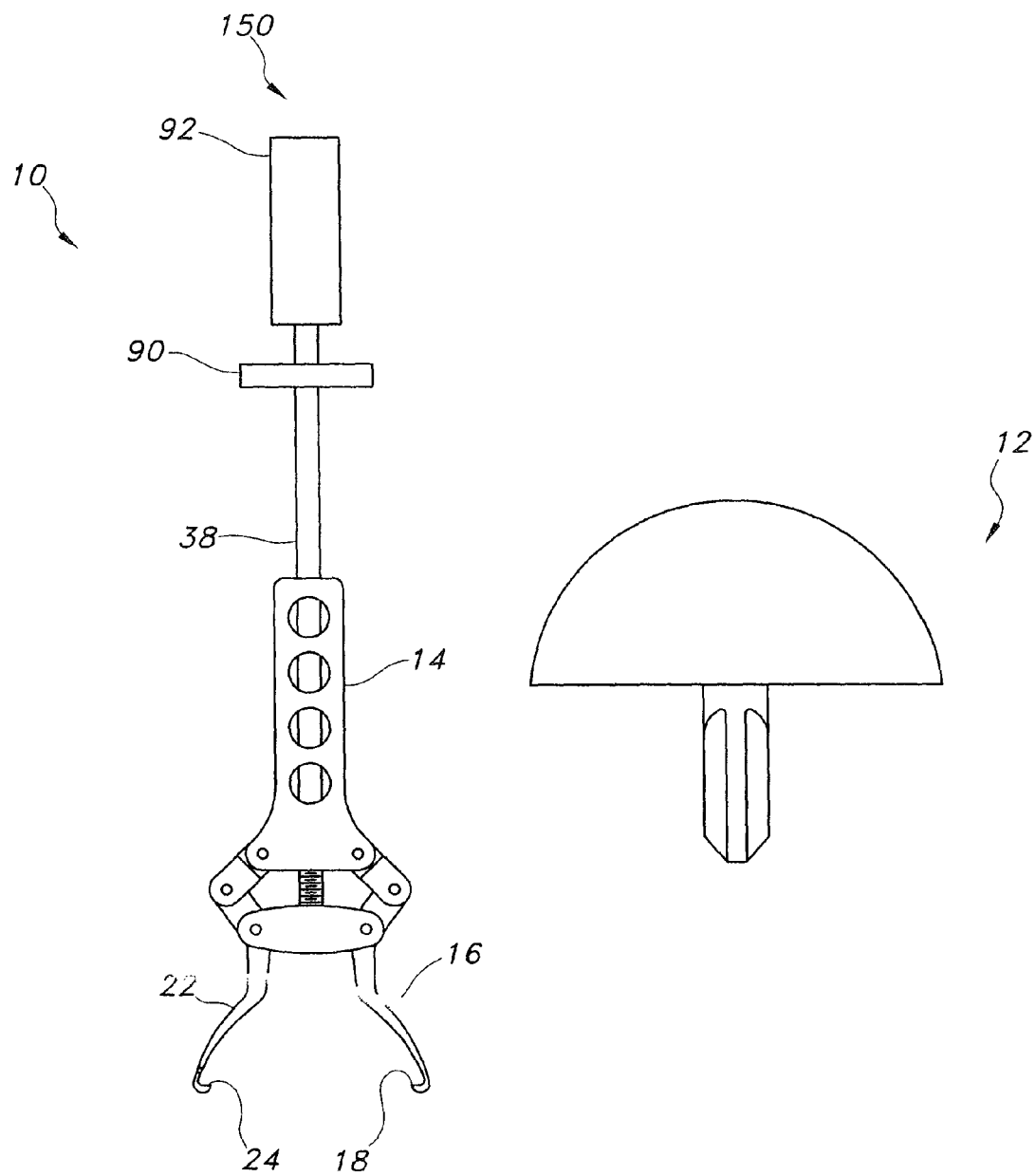
FIG. 13 is a plan view of a kit including the extractor of FIG. 1 and a conservative humeral shoulder prosthesis.

Referring now to FIG. 13, kit 150 is shown according to another embodiment of the present invention. The kit 150 includes the instrument 10 as well as the implant 12. It should be appreciated the kit may include the instrument 10 as well as a different implant for example, a femoral or other implant. The kit 150 may be placed in a standard instrument tray and the implant 12 may be individually packaged in a sterile container. Alternatively, the instrument 10 may be positioned with the implant 12 in a common container for example, an instrument tray. Typically, the kit 150 may also include other instrumentation, for example, the hammer 100 as well as trials (not shown) and additional instrument, for example, reamers and broaches and the like.

Figure 14:
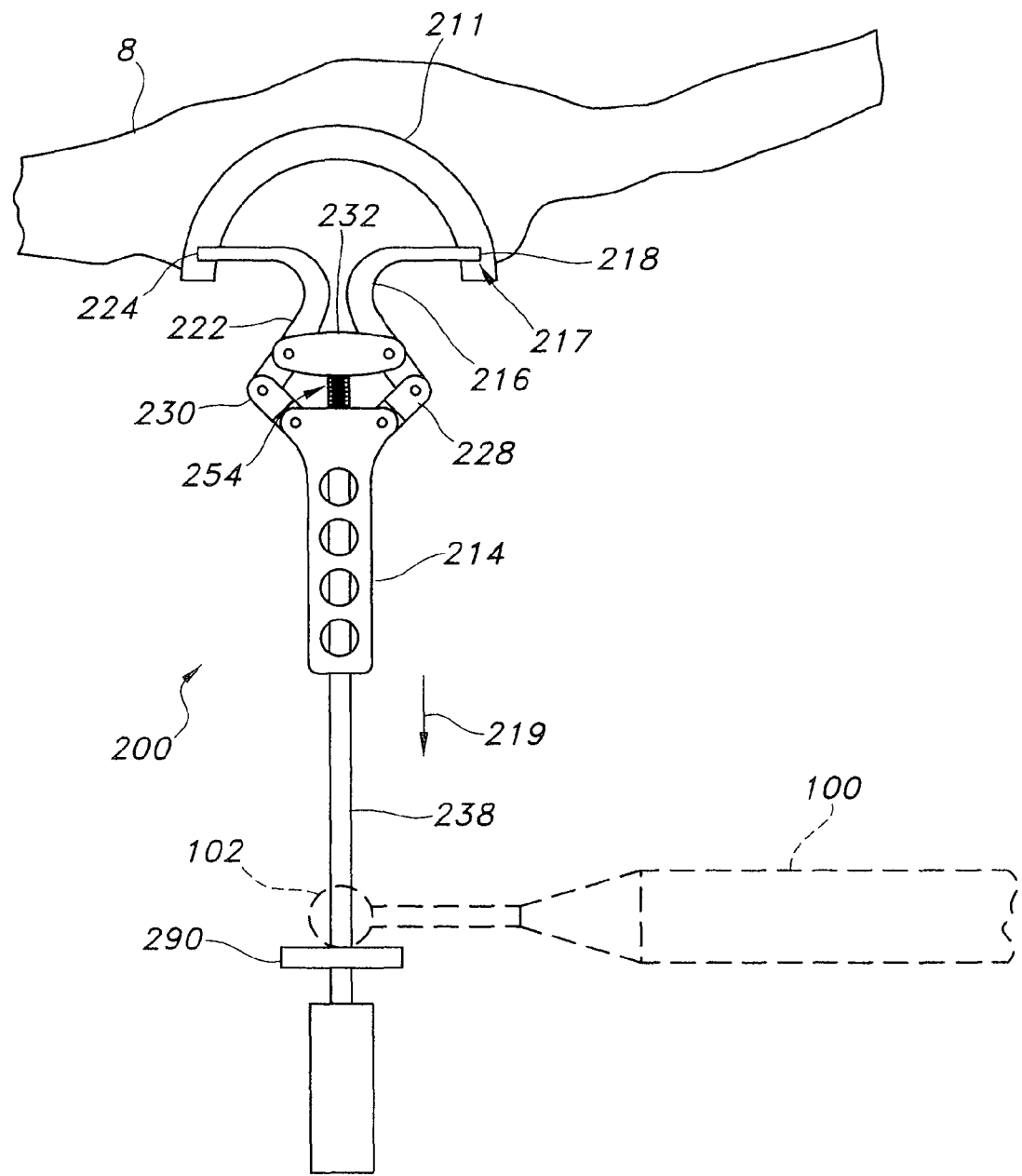
FIG. 14 is a plan view of another embodiment of the present invention in the form of an extractor for extracting an acetabular hip cup prosthesis.

Referring now to FIG. 14, another embodiment of the present invention is shown as instrument 200. The instrument 200, as is shown in FIG. 14, is utilized for insertion and removal of an implant 211 in the form of acetabular cup to be used with a hip prosthesis for implantation into the acetabulum 8 of a patient.

The instrument 200 is similar to the instrument 100 of FIGS. 1-7. For example, the instrument 200 includes a body 214, similar to the body 14 of the instrument 10, and a shaft 238. The shaft 238 is similar to the shaft 38 of FIG. 1-5 and rotatably and slidably cooperable with body 216. The shaft 238 includes a turnbuckle 254 similar to the turnbuckle 54 of the instrument 10. Turnbuckle 254 engages the third linking member 232 similarly to the third linking member 32 of the instrument 10 and causes the first member 216 supported by the first link 228 and the second member 222 supported by the third link 230 to advance to engage the implant 211.

For example and is shown in FIG. 14, the first member 216 engages a feature on the implant 211 for example, groove 217 at first contact portion 218 of the first member 216 while second contact portion 224 of the second member 222 also engages the groove 217 of the implant 211. When the members 216 and 222 are fully engaged with the implant 211, the instrument 200 is advanced in the direction of arrow 219 to permit the implant 211 to be removed from the acetabulum 8. A hammer, for example, hammer 100 may engage the shaft 238 of the instrument 200 with the head 102 of the hammer 100 striking collar 290 of the instrument 200.

Referring now to FIG. 15, yet another embodiment of the present invention is shown as instrument 300. Instrument 300 unlike instrument 10 and instrument 200 does not include a system of components that pivot and utilize linking members. The instrument 300 includes a body 314 that is unitary but resilient. The body 314 may be secured to the shaft, for example, a shaft 338 to which, for example, a collar 390 and handle 392 are secured. The body 318 includes an internal opening 315 into which the implant 12 may be placed. The body 314 may include a first contact portion 318 and a second spaced-apart contact portion 324. The contact portions 318 and 324 may be resiliently deflected over the outer periphery 19 of the implant 12. The portion 318 and 324 may then be resiliently positioned to engage outer face 17 of the implant 12. The collar 390 may be utilized to be struck by hammer 100 of FIG. 9 to advance the implant 12 into the direction of arrow 321 to permit removal of the implant 12 from the humerus 2.

Figure 15A:
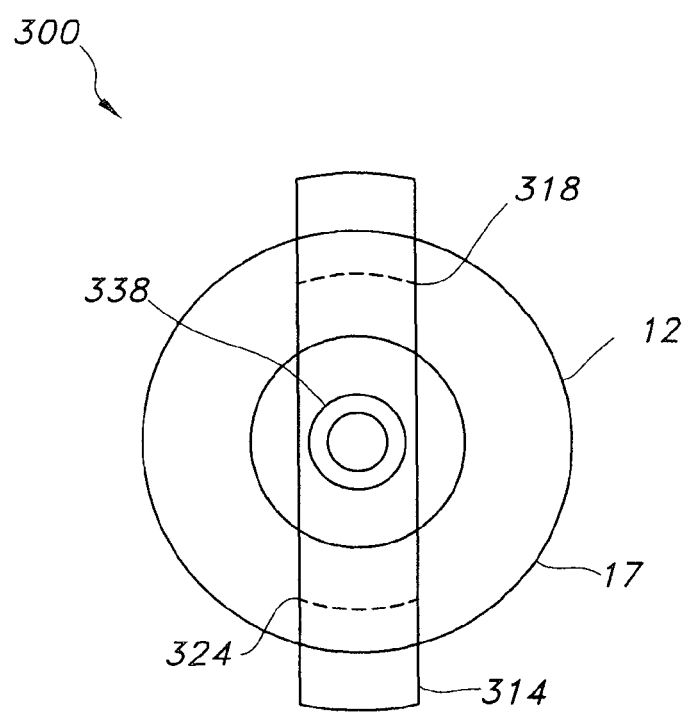
FIG. 15A is an end view of the pliable extractor of FIG. 15.

Referring now to FIG. 15A, the first and second contact portions 318 and 324 are shown in position over the implant 12. It should be appreciated that the contact portions 318 and 324 may cover only a portion of the contact surface 17 of the implant 12 or may cover substantially all of contact surface 17 of the implant 12.

Figure 16:
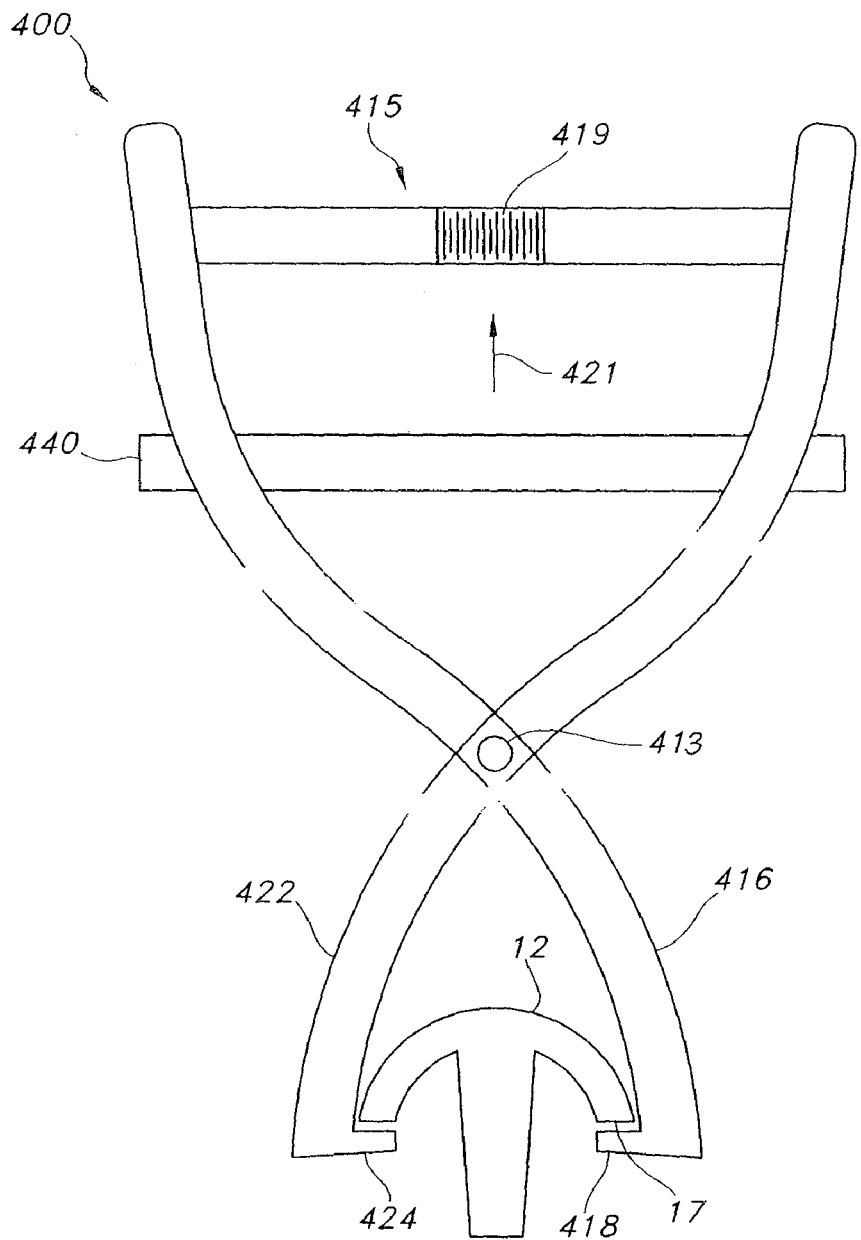
FIG. 16 is a plan view of another embodiment of the present invention in the form of a scissors type extractor for extracting a conservative humeral shoulder prosthesis.

Referring now to FIG. 16, another embodiment of the present invention is shown as instrument 400. Instrument 400 may be utilized repeatedly to remove implant 12 from humerus 2. The instrument 400 may include a first member 416 pivotally connected to a second member 422 to have general appearance of scissors. First member 416 and second member 422 may be connected, for example, by pin 413. A latching mechanism 415 may be secured to the first member 416 and the second member 422 to secure the members 416 and 422 into the engagement into the implant 12. The latching mechanism 415 may include engageable and disengageable teeth 419.

The first member 416 may include a first contact portion 418 while the second member 422 may include a second contact portion 424. The contact portion 418 and 422 may engage outer face 17 of the implant 12 to permit removal of the implant 12. A collar 490 may be secured to the members 416 and 422 for engagement with the hammer 100 for striking the collar 490 in the direction of arrow 421.

Figure 17:
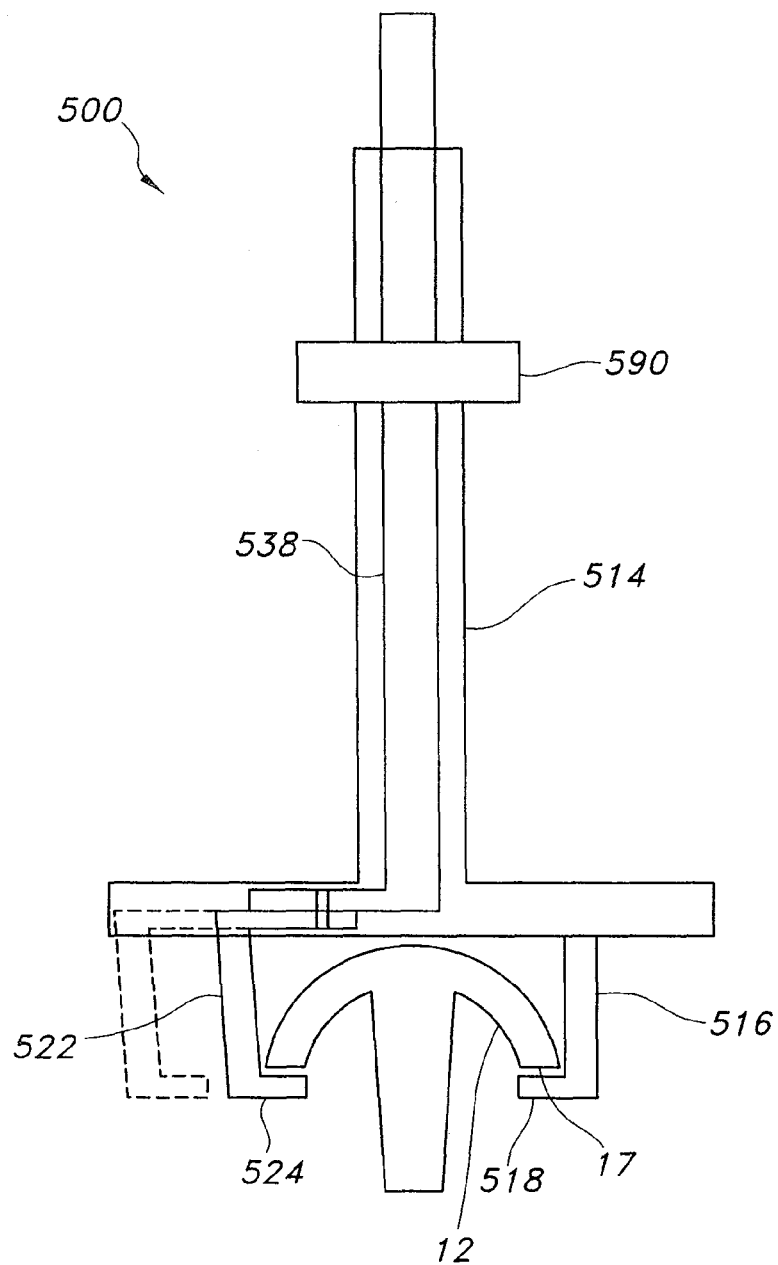
FIG. 17 is a plan view of an another embodiment of the present invention in the form of a cam-actuated extractor for extracting a conservative humeral shoulder prosthesis.
Figure 17A:
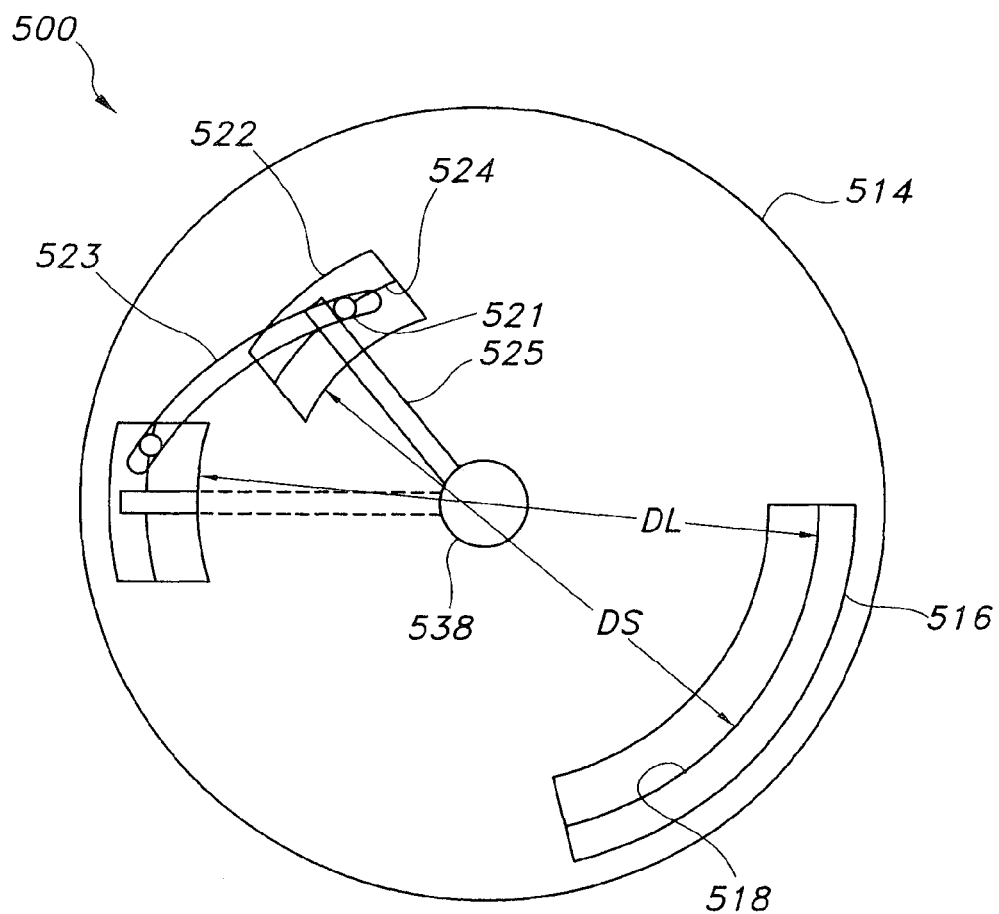
FIG. 17A is an end view of the cam-actuated extractor of FIG. 17.

Referring now to FIGS. 17 and 17A, yet another embodiment of the present invention is shown as instrument 500. Instrument 500 may include a body 514 to which first member 514 is rigidly attached and to which a second member 522 is movably attached. The second member 522 may be moveably attached to the body 514 by the means of pin 521 extending in a slot 523 formed in the body 514. The second member 522 may be moved along a slot 523 by a arm 525 extending from shaft 538 positioned with the body 514. As the shaft 538 is rotated with the body 514 the second member 522 may be advanced or retracted from the first member 516.

The first member 516 may include a first contact portion 518 while second member 522 may include a second contact portion 524. The contact portions 518 and 524 engage outer face 17 of the implant 12 to permit the removal of implant 12 from the humerus. A collar 590 may be positioned on the body 524 for assisting in the use of the hammer 100 to strike the collar 590 to remove the instrument 500 in the implant 12 from the humerus 2.

Figure 18:
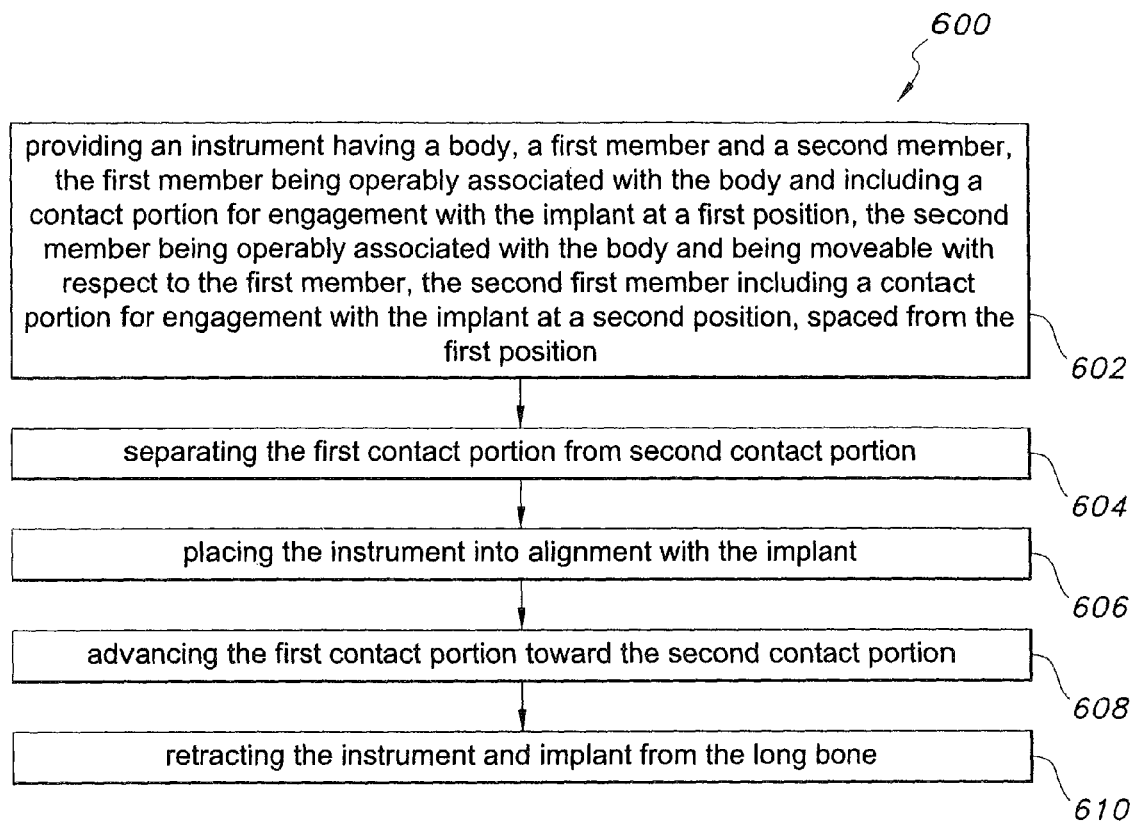
FIG. 18 is a flow chart of a method for performing arthroplasty in accordance with an embodiment of the present invention.

Referring now to FIG. 18, another embodiment of the present invention, is shown as surgical procedure or method 600 for removing a surface replacement implant from a long bone. The method 600 includes a first step 602 of providing an instrument having a body, a first member and a second member, the first member being operably associated with the body and including a contact portion for engagement with the implant at a first position, the second member being operably associated with the body and being moveable with respect to the first member, the second first member including a contact portion for engagement with the implant at a second position, spaced from the first position. The method 600 further includes a second step 604 of separating the first contact portion from the second contact portion. The method 600 further includes a third step 606 of placing the instrument into alignment with the implant. The method also includes the fourth stem 608 of advancing the first contact portion toward the second contact portion and the fifth stem 610 of retracting the instrument and implant from the long bone.

Although the present invention and its advantages have been described in detail, it should be understood that various changes, substitutions, and alterations can be made therein without departing from the spirit and scope of the present invention as defined by the appended claims.

We claim:

1. An instrument for use in removal of a prosthetic implant for use performing arthroplasty, comprising:
   a body;
   a first member connected to said body, said first member including a gripping contact portion for gripping engagement with an inner lip of the implant at a first position;
   a second member connected to said body, said second member being moveable with respect to said first member, said second member including a first gripping contact portion for gripping engagement with an inner lip of the implant at a second position, spaced from the first position, the gripping contact portions of the first and second members include a tine for gripping the inner lip of the implant; and
   an urging member for urging the contact portion of said first member toward the contact portion of said second member, wherein the urging member includes a first linking member pivotally coupled to the body and the first member, a second linking member pivotally coupled to the body and the second member, a third linking member coupled to the first and second linking members, and a shaft having a longitudinal axis and coupled to the third linking member, such that as the shaft is moved along the longitudinal axis, the first and second linking members pivot relative to the body, thereby causing the first and second members to pivot relative to the body;
   wherein at least one of the contact portion of said first member and contact portion of said second member is generally fork shaped having two spaced apart tines.

2. The instrument of claim 1, wherein at least one of said first member and second member is indirectly connected to said body.

3. The instrument of claim 1, wherein at least one of said first member and said second member includes a fulcrum about which said member pivots, the contact portion of said member being spaced from the fulcrum.

4. The instrument of claim 1, wherein at least one of the contact portion of said first member and contact portion of said second member is generally wedge shaped.

5. The instrument of claim 1, wherein at least one of said first member and said second member is moveable with respect to said other member to fixedly secure the implant there-between.

6. The instrument of claim 1, further comprising a hammer for striking the instrument to urge the instrument in a first direction.

7. The instrument of claim 1, further comprising:
   a first link pivotably connected to said urging member and to said first member;
   a second link pivotably connected to said urging member and to said second member; and
   a third member connected to said urging member and pivotably connected to said first member and to said second member, said urging member moveably connected to said body.

8. A kit for use in performing arthroplasty, said kit comprising:
   a prosthetic implant; and
   an instrument for use in removal of said prosthetic implant for use performing arthroplasty, the instrument including a body, a first member connected to said body, said first member including a gripping contact portion for gripping engagement with an inner lip of said implant at a first position, a second member connected to said body, said second member being moveable with respect to said first member, said second member including a gripping contact portion for gripping engagement with an inner lip of said implant at a second position, spaced from the first position, the gripping contact portions of the first and second members include a tine for gripping the inner lip of the implant, and an urging member for urging the contact portion of said first member toward the contact portion of said second member, wherein the urging member includes a first linking member pivotally coupled to the body and the first member, a second linking member pivotally coupled to the body and the second member, a third linking member coupled to the first and second linking members, and a shaft having a longitudinal axis and coupled to the third linking member, such that as the shaft is moved along the longitudinal axis, the first and second linking members pivot relative to the body, thereby causing the first and second members to pivot relative to the body; wherein at least one of the contact portion of said first member and contact portion of said second member is generally fork shaped having two spaced apart tines.

9. The kit of claim 8, further comprising a trial.

10. The kit of claim 8, further comprising a cutter for preparing a long bone for receiving said implant.

11. The kit of claim 8, further comprising:
    a first link pivotably connected to said urging member and to said first member;
    a second link pivotably connected to said urging member and to said second member; and
    a third member connected to said urging member and pivotably connected to said first member and to said second member, said urging member moveably connected to said body.

12. A method for removing a surface replacement implant from a long bone, the method comprising the steps of:
    using an instrument having a body, a first member and a second member and an urging member, the first member being the body and including a contact portion for engagement with the implant at a first position, the second member being the body and being moveable with respect to the first member, the second member including a contact portion for engagement with the implant at a second position, spaced from the first position, the urging member for urging the contact portion of said first member toward the contact portion of said second member and for urging the contact portion of said first member away from the contact portion of said second member, wherein the urging member includes a first linking member pivotally coupled to the body and the first member, a second linking member pivotally coupled to the body and the second member, a third linking member coupled to the first and second linking members, and a shaft having a longitudinal axis and coupled to the third linking member, such that as the shaft is moved along the longitudinal axis, the first and second linking members pivot relative to the body, thereby causing the first and second members to pivot relative to the body; wherein at least one of the contact portion of said first member and contact portion of said second member is generally fork shaped having two spaced apart tines;

utilizing the urging member to separate the first contact portion from the second contact portion;

placing the instrument into alignment with the implant;

advancing the first contact portion toward the second contact portion with the urging member;

gripping an inner lip of the implant with the first and second contact portions; and retracting the instrument and implant from the long bone.

* * * * *